(12) United States Patent
Bis et al.

(10) Patent No.: US 9,643,950 B2
(45) Date of Patent: May 9, 2017

(54) SOLID FORMS OF {S-3-(4-AMINO-1-OXO-ISOINDOLIN-2-YL)(PIPERIDINE-3,4,4,5,5-D$_5$)-2,6-DIONE}

(71) Applicant: Concert Pharmaceuticals, Inc., Lexington, MA (US)

(72) Inventors: Joanna A. Bis, Cary, NC (US); David H. Igo, Raleigh, NC (US)

(73) Assignee: Concert Pharmaceuticals, Inc., Lexington, MA (US)

(*) Notice: Subject to any disclaimer, the term of this patent is extended or adjusted under 35 U.S.C. 154(b) by 0 days.

(21) Appl. No.: 14/437,519

(22) PCT Filed: Oct. 21, 2013

(86) PCT No.: PCT/US2013/065929
§ 371 (c)(1),
(2) Date: Apr. 22, 2015

(87) PCT Pub. No.: WO2014/066243
PCT Pub. Date: May 1, 2014

(65) Prior Publication Data
US 2015/0299162 A1 Oct. 22, 2015

Related U.S. Application Data

(60) Provisional application No. 61/716,826, filed on Oct. 22, 2012.

(51) Int. Cl.
*C07D 401/04* (2006.01)
*A61K 31/454* (2006.01)
*C09K 3/00* (2006.01)

(52) U.S. Cl.
CPC .............. *C07D 401/04* (2013.01); *C09K 3/00* (2013.01); *C07B 2200/13* (2013.01)

(58) Field of Classification Search
CPC ............................ C07D 401/04; A61K 31/454
USPC .......................................... 546/201; 514/323
See application file for complete search history.

(56) References Cited

U.S. PATENT DOCUMENTS

| | | |
|---|---|---|
| 5,635,517 A | 6/1997 | Muller et al. |
| 6,221,335 B1 | 4/2001 | Foster |
| 6,281,230 B1 | 8/2001 | Muller et al. |
| 6,440,710 B1 | 8/2002 | Keinan et al. |
| 6,603,008 B1 | 8/2003 | Ando et al. |
| 7,517,990 B2 | 4/2009 | Ito et al. |
| 8,288,414 B2 | 10/2012 | Czarnik |

(Continued)

FOREIGN PATENT DOCUMENTS

| | | |
|---|---|---|
| CN | 102453021 * | 5/2012 |
| WO | 95/26325 A2 | 10/1995 |

(Continued)

OTHER PUBLICATIONS

Dean "Analytical chemistry handbook" p. 10.24-10.26 (1993).*

(Continued)

*Primary Examiner* — Celia Chang
(74) *Attorney, Agent, or Firm* — McCarter & English, LLP; Steven G. Davis; Wei Song

(57) ABSTRACT

The invention in one embodiment is directed to solid forms of {S-3-(4-Amino-1-oxo-isoindolin-2-yl)(piperidine-3,4,4,5,5-d$_5$)-2,6-dione}, including an anhydrous crystalline form, two hydrates, and an amorphous form. The invention in one embodiment is directed to methods of preparation of the solid forms.

3 Claims, 15 Drawing Sheets

(56) References Cited

U.S. PATENT DOCUMENTS

| | | | |
|---|---|---|---|
| 9,045,453 | B2 | 6/2015 | Tung |
| 2003/0096841 | A1 | 5/2003 | Robarge et al. |
| 2007/0082929 | A1 | 4/2007 | Gant et al. |
| 2007/0191432 | A1 | 8/2007 | Tung |
| 2007/0197695 | A1 | 8/2007 | Potyen et al. |
| 2008/0103122 | A1 | 5/2008 | Veltri |
| 2008/0108608 | A1 | 5/2008 | Jones et al. |
| 2008/0194617 | A1 | 8/2008 | Tawaraishi et al. |
| 2009/0069379 | A1 | 3/2009 | Czarnik |
| 2011/0071074 | A1 | 3/2011 | Perni et al. |
| 2015/0336927 | A1 | 11/2015 | Tung |

FOREIGN PATENT DOCUMENTS

| | | | |
|---|---|---|---|
| WO | 9803502 | A1 | 1/1998 |
| WO | 2006089150 | A2 | 8/2006 |
| WO | 2007118651 | A1 | 10/2007 |
| WO | 2009114601 | | 9/2009 |
| WO | 2010056344 | A1 | 5/2010 |
| WO | WO2010/056344 | * | 5/2010 |
| WO | WO2010056344 | * | 5/2010 |
| WO | 2010061209 | A1 | 6/2010 |
| WO | 2010093434 | A1 | 8/2010 |
| WO | 2010093605 | A1 | 8/2010 |
| WO | 2011069608 | A1 | 6/2011 |
| WO | 2012015986 | A2 | 2/2012 |
| WO | 2012079022 | A1 | 6/2012 |
| WO | 2012079075 | A1 | 6/2012 |
| WO | 2013130849 | A1 | 9/2013 |

OTHER PUBLICATIONS

"Solvent" Wikipedia, p. 1-10 (2011).*
US Pharmaceopeia "national formulary" p. 1843-44 (1994).*
Exhibit 1 "side-by-side" p. 1 (2016).*
Blomquist, Alfred, et al., Deuterated Amino Acids. III. Synthesis of DL-aspartic-2,3,3-d3 Acid, L-Glutamic-2,3,3,4,4-d5 Acid, Lasparagine-2,3,3-d3, and L-Glutamine-2,3,3,4,4-d5, Journal of Organic Chemistry, 31 (12):4121-4127, 1966.
International Search Report for PCT/US2013/028379, Aug. 2, 2013.
Written Opinion for PCT/US2013/028379, Aug. 2, 2013.
FDA Label, Revlimid-lenalidomide capsule; For Multiple Myeloma Myelodysplastic Syndrome and Mantle Cell Lymphoma; 47 pp; revised Sep. 2014.
"Lenalidomide in acute myeloid leukemia" from Clinical Studies Data accessed on Jan. 8, 2015.
Lenalidomide in acute myeloid leukemia: The NCT02126553 study from Clinical Studies Data accessed on Jan. 8, 2015.
Lenalidomide in amyloid light-chain amyloidosis from Clinical Studies Data accessed on Jan. 8, 2015.
Lenalidomide and dexamethasone in amyloidosis associated end-stage renal disease/dialysis: The NCT00091260 study from Clinical Studies Data accessed on Jan. 8, 2015.
Lenalidomide in follicular lymphoma: The NCT01180569 study from Clinical Studies Data accessed on Jan. 8, 2015.
Lenalidomide plus rituximab in follicular lymphoma from Clinical Studies Data accessed on Jan. 8, 2015.
Lenalidomide in chronic lymphocytic leukemia from Clinical Studies Data accessed on Jan. 8, 2015.
Lenalidomide in chronic lymphocytic leukemia from Clinical Studies Data accessed Jan. 8, 2015.
Lenalidomide in Hodgkin's lymphoma from Clinical Studies Data accessed on Jan. 8, 2015.
Lenalidomide in Hodgkin's lymphoma: The NCT00540007 study from Clinical Studies Data accessed on Jan. 8, 2015.
Lenalidomide in glioma: The NCT01222754 study from Clinical Studies Data accessed on Jan. 8, 2015.
Lenalidomide in diffuse large B-cell lymphoma from Clinical Studies Data accessed on Jan. 8, 2015.
Lenalidomide, rituximab, cyclophosphamide, vincristine, doxorubicin and prednisone in diffuse large B-cell/follicular lymphoma: The NCT00670358 study from Clinical Studies Data accessed on Jan. 8, 2015.
Lenalidomide in chronic myelomonocytic leukemia: The NCT01368757 study from Clinical Studies Data accessed on Jan. 8, 2015.
Lenalidomide in non-Hodgkin's lymphas from Clinical Studies Data accessed on Jan. 8, 2015.
Dexamethasone, lenalidomide, and rituximab in variable regimens in non-Hodgkin's B-cell lymphoma from Clinical Studies Data accessed on Jan. 8, 2015.
Lenalidomide Maintenance Therapy in Stage IIIB/IV Non-small Cell Lung Cancer from ClinicalTrials.gov accessed on Jan. 8, 2015.
Lenalidomide in T-cell non-Hodgkin's lymphoma: The NCT00322985 study from Clinical Studies Data accessed on Jan. 8, 2015.
Lenalidomide, romidepsin, and dexamethasone in variable regimens in Hodgkin's lymphoma/mature T-cell lymphoma/multiple myeloma: The RID; NCT01742793 study from Clinical Studies Data accessed on Jan. 8, 2015.
Lenalidomide in Waldenstrom's macroglobulinemia: The NCT02302469 study from Clinical Studies Data accessed on Jan. 8, 2015.
Lenalidomide, rituximab, cyclophosphamide and dexamethasone in non-Hodkin's lymphoma/Waldenstrom's macroglobulinemia accessed on Jan. 8, 2015.
Wermuth The Practice of Med Chem 1996, pp. 203-237.
Baille, T. A., "The Use of Stable Isotopes in Pharmacological Research," Pharmacological Reviews, 33(2): 81-132 (1981).
Browne, T. R., "Stable Isotope Techniques in Early Drug Development: An Economic Evaluation," J. Clin. Pharmacol., 38: 213-220 (1998).
Cherrah, Y., et al., "Study of Deuterium Isotope Effects on Protein Binding by Gas Chromatography/Mass Spectrometry. Caffeine and Deuterated Isotopomers," Biomedical and Environmental Mass Spectrometry, 14: 653-657 (1987).
Dyck, L. E., et al., "Effects of Deuterium Substitution on the Catabolism of ?-Phenylethylamine: An In Vivo Study," Journal of Neurochemistry, 46(2): 399-404 (1986).
Foster, A. B. "Deuterium Isotope Effects in Studies of Drug Metabolism," Trends in Pharmacological Sciences, 5: 524-527 (1984).
Foster, A. B., "Deuterium Isotope Effects in the Metabolism of Drugs and Xenobiotics: Implications for Drug Design," Advances in Drug Research, 14: 1-40 (1985).
Gouyette, A., "Synthesis of Deuterium-labelled Elliptinium and its Use in Metabolic Studies," Biomedical and Environmental Mass Spectrometry, 15: 243-247 (1988).
Haskins, N. J., "The Application of Stable Isotopes in Biomedical Research," Biomedical Mass Spectrometry, 9(7): 269-277 (1982).
Honma S., et al., "The Metabolism of Roxatidine Acetate Hydrochloride," Drug Metabolism and Disposition, 15(4): 551-559 (1987).
Peiniaszek, H. J., et al., "Moricizine Bioavailability via Simultaneous, Dual, Stable Isotope Administration: Bioequivalence Implications," J. Clin. Pharmacol, 39: 817-825 (1999).
Tonn G. R., et al., "Simultaneous Analysis of Diphenhydramine and a Stable Isotope Analog (2H10) Diphenhydramine Using Capillary Gas Chromatography with Mass Selective Detection in Biological Fluids from Chronically Instrumented Pregnant Ewes," Biological Mass Spectrometry, 22: 633-642 (1993).
Wolen, R. L., "The Application of Stable Isotopes to Studies of Drug Bioavailability and Bioequivalence," J. Clin. Pharmacol., 26: 419-424 (1986).
Fisher, M.B. et al., "The Complexities Inherent in Attempts to Decrease Drug Clearance by Blocking Sites of CYP-Mediated Metabolism," Curr. Opin. Drug Discov. Devel., 9(1):101-109 (2006).
Kushner, D.J. et al., "Pharmacological Uses and Perspectives of Heavy Water and Deuterated Compounds," Can. J. Physiol. Pharmacol., 77:79-88 (1999).
Center for Drug Evaluation and Research, Pharmacology/toxicology Review and Evaluation; Apr. 7, 2005, 191pp.

(56) References Cited

OTHER PUBLICATIONS

Reist, M., Chiral Inversion and Hydrolysis of Thatlidmide: Mechanisms and Catalysis by Baes and Serum Albumin, and Chiral Stability of Teratogenic Metabolites; Chem. res. Toxicol.; 11:1521-1528; 1998.
Maltais, F., In Vitro and In Vivo Isotope Effects with Hepatitis C Protease Inhibitors: Enhanced Plasma Exposure of Deuterated Telaprevir versus Telaprevir in Rats; J. Med. Chem., 52:7993-8001; 2009.
Yamamoto, T., et al., Synthesis and Configurational Stability of (S)-and (R)-deuteriothalidomides, Chem. Pharm. Bull; 58(1):110-112; 2010.
Science IP Search Results for Lenalidomide, CAS Chemcals database, 5pp, 2012.
Corral, L.G., et al., Differential Cytokine Modulation and T Cell Activation by Two Distinct Classes of Thalidomide Analogues that Are Potent Inhibitors of TNF-{alpha}; J. Immunol. 163:380-386; 1999.
Li, R., et al., Racemization of Vinylglycolate Catalyzed by Mandelate Racemase, J. Org. Chem., 60:3347-3351, 1995.
Eriksson, T., et al., Intravenous Formulations of the Enantiomers of Thalidomide: Pharmacokinetic and Initial Pharmacodynamic Characterization in Man; J. Pharm. Pharmacol., 52:807-817; 2000.
Eriksson, T., et al., Stereospecific Determination, Chiral Inversion In Vitro and Pharmacokinetics in Humans of the Enantiomers of Thalidomide; Chirality 7:44-51, 1995.
Eriksson, T., et al., Enantiomers of Thalidomide: Blood Distribution and the Influence of Serum Albumin on Chiral Inversion and Hydrolysis, Chirality, 10:223-228; 1998.
Pal, R., et al., Immunomdoulatory Derivatives Induce PU.1 Down-Regulation, Myeloid Maturation Arrest, and Neutropenia, Blood, 115(3):605-614; Jan. 21, 2010.
Kumar, G., et al., Lenalidomide: In Vitro Evaluation of the Metabolism and Assessment of Cytochrome P450 Inhibition and Induction; Cancer chemother Pharmacol; Nov. 23, 2008.
Highlights of Prescribing Information; REVLLIMID® 2005.
Richardson, P.G., et al., Lenalidomide in Multiple Myeloma; Drug Profile, 1165-1173, 2006.
Schreck, D.M., et al., Comparison of Racemic Albuterol and Levalbuterol in the Treatment of Acute Ashtma in the ED, American Journal of Emergency Medicine; 23:842-847, 2005.
Stoschitzky, K., et al., Racemic (R,S)-propranolol Versus Half-Dosed Optically Pure (S)-Propranolol in Humans at Steady State: Hemodynamic Effects, Plasma Concentrations, and Influence on Thyroid Hormone Levels, Clin Pharmacol. Ther 51:445-453; 1992.
Anderson, G., et al., Thalidomide Derivative CC-4047 Inhibits Osteoclast Formation by Down-Regulation of PU.1; Blood, 107(8):3098-3105, Apr. 15, 2006.

International Search Report for PCT/US2011/045629, 4PP, Mar. 15, 2012.
Written Opinion of PCT/US2011/045629; 5 pp, Mar. 15, 2012.
Internationl Search Report of PCT/US09/06105; 1 page, Jan. 25, 2010.
International Preliminary Report on Patentability for PCT/US09/06105; 4pp, May 17, 2011.
Maltais, F., In Vitro and In Vivo Isotope Effects with Hepatitis C Protease Inhibitors: Enhanced Plasma Exposure of Deuterated Telaprevir versus Telaprevir in Rats; Abstract; http://pubs.acs.org/doi/abs/10.1021/jm90102; Nov. 6, 2009.
Highlights of Prescribing Information, REVLIMID®, 27pp, Mar. 2012.
Chen, Nianhang, et al., Pharmacokinetics metabolism and exertion of [14C]-lenalidomide following oral administration in health male subjects, Cancer Chemother. Pharmacol., 69(3):789-787, 2011.
Extended European Search Report for Related European Application No. 09826438.5, May 18, 2012.
Rhodes, Harold J., et al., Synthesis of 2,6-Dioxo-3-phthalimidopiperidine-3,4,4,5,5,-d, and 2,5-Dioxo-3-phthalimidopyrrolidine-3,4,4-d, from L-Deuterio-Glutamic Acid and L-Deuterio-Aspartic Acid, Journal of Pharmaceutical Sciences, 54(10):1440-1443, Oct. 1965.
He, Yihui, et al., Prospects for the Pharmacologica use of Heavy Water and Deuterium-Containing Drugs, Foreign Medical Sciences Epidemiology Lemology, 32(4):255-256; Aug. 2005.
International Search Report for PCT/US2011/064409, Mar. 23, 2012.
Written Opinion for PCT/US2011/064409, Mar. 23, 2012.
Tefferi, Ayalew, et al., "Pomalidomide is Active inthe Treatment of Anemia Associated with Myelofibrosis", Journal of Clinical Oncology, 27(27):4563, 2009.
Concert Pharmaceuticals, et al, Precision Deuterium Chemistry Backgrounder, http://www.webictation.org/5e81SGCn1, pp. 1-6, 2007.
Buteau, K.C., Deuteraed Drugs: Unexpectedly Nonobvious?, Journal of High Technology Law, Suffical University Law School, X(1):22-74; Jan. 2009.
International Search Report for PCT/US2011/064238, Feb. 27, 2012.
Written Opnion for PCT/US2011/064238, Feb. 27, 2012.
Ducho, C., et al., Synthesis of Regio-and Stereoselectivly Deuterium-Labelled Derivatives of L-Glutamate Semialdehyde for Studies on Carbapenem Biosynthesis, Organic & Biomolecular Chemistry, Royal Society of Chemistry, 7(11):2773, May 11, 2009.
Michalska, Danuta, The Raman and IR Spectra and Normal Coordinate Analysis of 3-(N-phenylacetylamino)-2,6-Piperidinedion e, Antineoplaston A10, the New Antitumor Drug, Spectrochimica Acta. Part A: Molecular and Biomolecular Spectroscopy, 49a(3):303-314, 1993.

* cited by examiner

DSC/TGA of Form 4 D-(S)-lenalidomide made by Lyophilization

SOLID FORMS OF {S-3-(4-AMINO-1-OXO-ISOINDOLIN-2-YL)(PIPERIDINE-3,4,4,5,5-D$_5$)-2,6-DIONE}

RELATED APPLICATIONS

This application is a 35 U.S.C. §371 national stage filing of International Application No. PCT/US2013/065929, filed Oct. 21, 2013, which claims the benefit of U.S. Provisional Patent Application No. 61/716,826, filed Oct. 22, 2012. The entire contents of each of the foregoing applications are hereby incorporated by reference.

BACKGROUND

Lenalidomide, chemically known as either 3-(4-amino-1,3-dihydro-1-oxo-2H-isoindol-2-yl)-2,6-piperidinedione or 3-(4-amino-1-oxo 1,3-dihydro-2H-isoindol-2-yl)piperidine-2,6-dione, and its pharmaceutically acceptable salts thereof are immunomodulatory agents. Lenalidomide has been shown to inhibit the secretion of pro-inflammatory cytokines such as tumor necrosis factor alpha (TNF-α) and to increase the secretion of anti-inflammatory cytokines in animals and humans. Decreasing TNF-α levels is a valuable therapeutic strategy for the treatment of many inflammatory, infectious, immunological, and malignant diseases (PCT publication WO 98/03502). Lenalidomide has been demonstrated to be useful in the treatment of anemia due to myelodysplastic syndromes associated with a deletion 5q cytogenic abnormality, as well as in the treatment of multiple myeloma when used in combination with dexamethasone.

It is known in the art that deuterated compounds, such as lenalidomide, may have an advantageous effect on metabolic properties such as absorption, distribution, metabolism and excretion of drug (ADME) without adversely altering pharmacologic properties.

SUMMARY OF THE INVENTION

The present invention is directed to novel solid forms of the deuterated S-enantiomer of lenalidomide of Formula I:

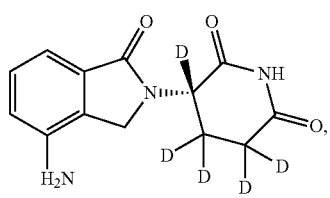

Formula I which is disclosed in PCT patent publication no. WO2010/056344.

The compound of Formula I shall also be referred to herein as D-(S)-lenalidomide.

In one aspect, the invention is directed to Form 1 D-(S)-lenalidomide.

In another aspect, the invention is directed to Form 2 D-(S)-lenalidomide.

In a further aspect, the invention is directed to Form 3 D-(S)-lenalidomide.

In still another aspect of the invention, the invention is directed to amorphous D-(S)-lenalidomide.

Throughout this application, unless otherwise specified, when a particular position is designated as having deuterium, it is understood that the abundance of deuterium at that position has a minimum isotopic enrichment factor of at least 3340 times the natural abundance of deuterium (50.1% deuterium incorporation) at each atom designated as deuterium in said compound. Preferably, the percentage of deuterium incorporation is at least 80%, at least 85%, at least 90%, at least 95%, at least 98%, or at least 99%.

DETAILED DESCRIPTION

Figure 1:
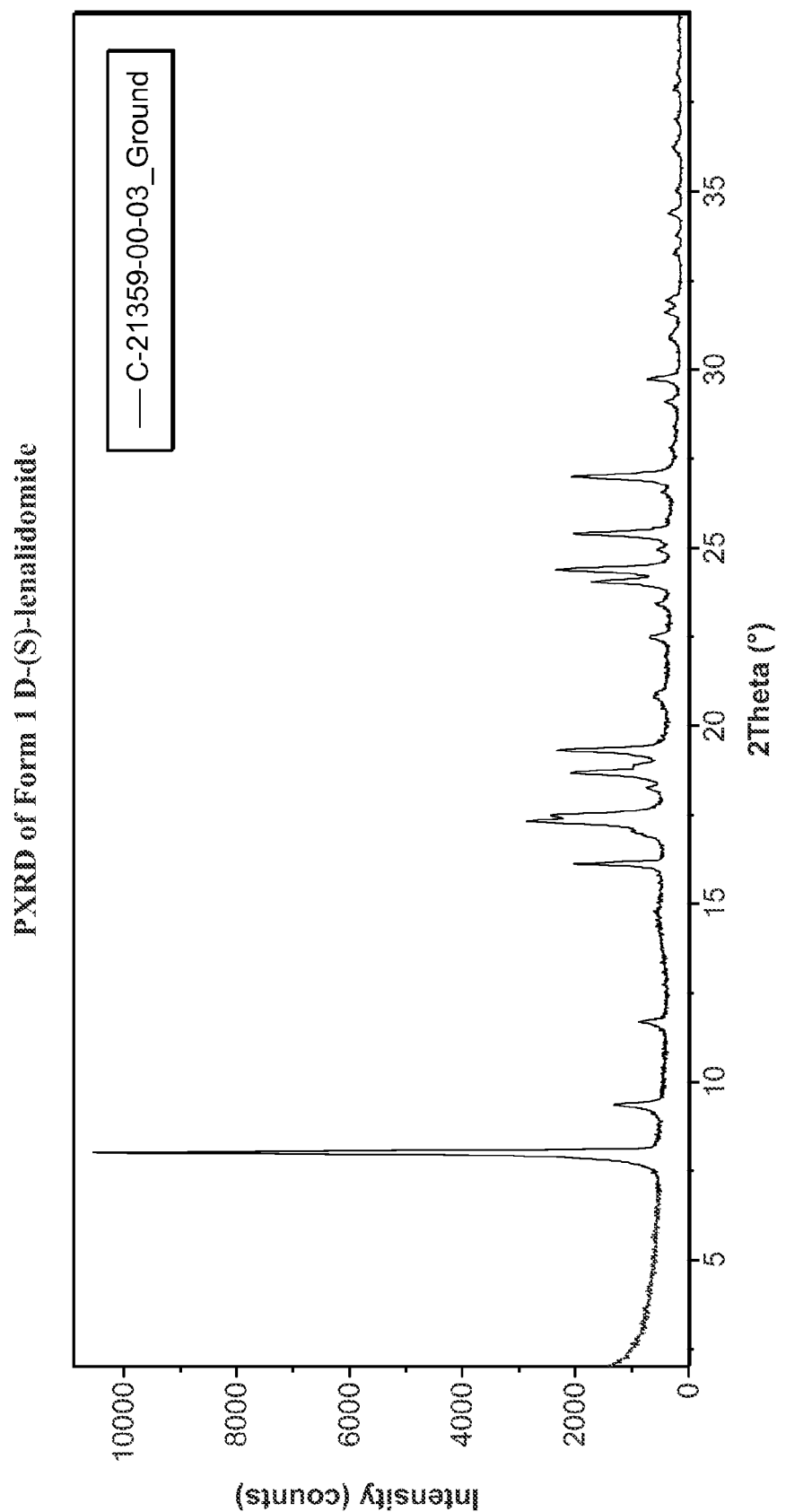
FIG. 1 is a powder x-ray diffraction ("PXRD") pattern of Form 1 of D-(S)-lenalidomide.

It is well established that solid-state properties of compounds can significantly affect their ability to become viable commercially such as by way of becoming an active pharmaceutical or nutraceutical ingredient in a formulated product. Properties, such as solubility, chemical stability, and physical stability, are known to vary, often significantly, between different solid forms of a compound.

The term "solid form" is often used to refer to a class or type of solid-state material. For example, the term "polymorph" when used to describe solid-state compounds refers to two or more compounds having the same chemical formula but differing in crystalline solid-state structure. Polymorphs of molecular compounds, such as active pharmaceutical ingredients, are often prepared and studied in order to identify compounds meeting scientific or commercial needs including, but not limited to improved solubility, dissolution rate, hygroscopicity, and stability.

The term "Form" as used herein is meant as a label to identify a Form. When used in connection with the compound of Formula I, it has the meaning set forth herein which includes characteristic features associated with Table 1.

Other solid forms include solvates and hydrates. A solvate is a compound wherein a solvent molecule is present in the crystal structure together with another compound. When the solvent is water, the solvent is termed a hydrate. Solvates and hydrates may be stoichiometric or non-stoichiometric. A stoichiometric hydrate is one where, in a crystalline form, the unit cell contains a defined ratio of the number of water molecules to the number of molecules of the active pharmaceutical ingredient. In a crystalline dihydrate, for example, in the unit cell of the crystal, the ratio of water molecules to active pharmaceutical ingredient molecules is 2:1. Form 3 of D-(S)-lenalidomide is a dihydrate.

The term "crystalline", as used herein, refers to a compound in the crystalline solid state. Forms 1 and 3 are crystalline. Form 2 has crystalline and amorphous characteristics. The remaining form disclosed herein is amorphous (also referred to herein as "Form 4").

Analytical techniques are commonly used to detect and analyze solid forms such as crystalline solid forms. Such techniques include single-crystal x-ray powder diffraction, powder x-ray diffraction, Raman spectroscopy, infrared spectroscopy, polarized light microscopy (PLM), solid-state nuclear magnetic resonance spectroscopy, and thermal measurements such as differential scanning calorimetry (DSC) which may be used to measure melting point.

The data generated when analyzing a solid form may be used to characterize or further characterize that form. For example, a powder-x-ray diffraction pattern may be used to characterize a crystalline form. A smaller subset of such data, however, may also be suitable for characterizing a crystalline form. For example, a collection of one or more peaks from such a pattern may be used to characterize a crystalline form.

An x-ray powder diffraction plot is an x-y graph with degrees-two theta (diffraction angle) on the x-axis and intensity on the y-axis. The peaks within this plot may be used to characterize a crystalline solid form. The data is often represented by the position of the peaks on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the pharmaceutical arts to characterize crystalline forms.

As with any data measurement, there is variability in x-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same crystalline solid form. Likewise, different software packages process x-ray data differently and this also leads to variability. These and other sources of variability are known to those of ordinary skill in the pharmaceutical arts. Due to such sources of variability, it is common to recite x-ray diffraction peaks using the word "about" prior to the peak value in ° 2Θ which, typically, presents the data to within 0.1 or 0.2 degrees two-theta of the stated peak value depending on the circumstances. All x-ray powder diffraction peaks cited herein have are reported with a variability on the order of 0.2 degrees two-theta and are intended to be reported with such a variability whenever disclosed herein whether or not the term "about" is used.

Raman spectroscopy is another technique that may be used to characterize solid forms together with or separately from x-ray powder diffraction. As with x-ray powder diffraction plots, peaks in a Raman spectrum are recorded by reference to their x-axis (wavenumber) position rather than their intensity. Variation in the position of Raman peaks also exists and may be due to sample conditions as well as data collection and processing. The typical variability in Raman spectra reported herein is on the order plus or minus 2.0 cm$^{-1}$. Thus, the use of the word "about" when referencing Raman peaks is meant to include this variability and all Raman peaks disclosed herein are intended to be reported with such variability whether or not the term "about" is expressly used.

Thermal methods are another typical technique to characterize solid forms. Different crystalline forms of the same compound often melt at different temperatures. Thus, for example, the melting point of a crystalline form, as measured by methods such as capillary melting point, DSC, and hot stage microscopy, alone or in combination with techniques such as x-ray powder diffraction, Raman spectroscopy, or IR spectroscopy (discussed below), or a combination of the foregoing, may be used to characterize crystalline forms.

As with any analytical technique, melting points determinations are also subject to variability. Common sources of variability, in addition to instrumental variability, are due to colligative properties such as the presence of other solid forms or other impurities within a sample whose melting point is being measured. All melting points cited herein are reported with a variability on the order of 4° C. and are intended to be reported with such a variability whenever disclosed herein whether or not the term "about" is used.

The invention is directed to four different solid forms of deuterated lenalidomide of Formula I. Forms 1, 2, and 3 are crystalline forms of the S-enantiomer of deuterated lenalidomide of Formula I whereas the remaining solid form disclosed herein is an amorphous solid form.

Each of the solid forms has been further characterized by several solid-state analytical techniques.

Examples of solid-state analytical techniques that can be used to characterize solid-state structure including single crystal x-ray diffraction, powder x-ray diffraction, solid-state $^{13}$C NMR, Raman spectroscopy, and thermal techniques such as Differential Scanning calorimetry (DSC) for identifying melting temperatures and other thermal events.

Solid-state data is typically used to characterize a polymorph of a compound so as to aid in identifying it and further distinguish it from other known polymorphs. To characterize a polymorph of a compound, one may, for example, collect x-ray powder diffraction data on different polymorphs of the compound and compare the x-ray powder diffraction peaks of the forms. When only two polymorphic forms—A and B—are compared and one finds a peak in a Form A pattern at an angle where no peaks appear in the Form B pattern, then that peak, for that chemical compound, distinguishes Form A from Form B and further acts to characterize Form A. When more polymorphic forms are present, then the same analysis is also done for the other forms. Thus, to characterize Form A against the other polymorphic forms, one would look for peaks in Form A at degrees two-theta values not present in the x-ray powder diffraction patterns of the other polymorphic forms. Although all the peaks within an entire diffractogram may be used to characterize such a form, one may instead, and typically does as disclosed herein, use a subset of that data to characterize the form.

When there are multiple forms which are not polymorphs of one another but possess characteristics that are not based on solid-state analytical techniques, those other characteristics can be used to differentiate and thus characterize the solid forms. For example, one can distinguish an anhydrous crystalline form of a compound from a monohydrate of that compound by the fact that the monohydrate has a different composition than the anhydrous crystalline form due to the presence of water. Thus, the presence (or absence) of water of hydration can be used to distinguish, and thus characterize a solid form. The fact that both forms may share the same peak in their respective x-ray powder diffraction patterns does not limit the utility of that peak because the forms can be differentiated based on their chemical composition (hydrate v. anhydrous). Other characteristics for characterizing and differentiating solid forms may include chirality and degree of crystallinity. These limitations can also be used together with solid-state analytical techniques if desired or convenient to characterize such solid forms.

In the invention herein, there is only one solid form directed to an anhydrous crystalline form of D-(S)-lenalidomide, Form 1. Thus, no additional solid-state analytical data are necessary to characterize this form with respect to Forms 2 through 4. Table 1 summarizes these characterizations.

TABLE 1

Non-Analytical Data-Based Characterizations

| Form | Characteristic |
|---|---|
| Form 1 | anhydrous; crystalline; D-(S)-lenalidomide |
| Form 2 | metastable hydrate; partially crystalline and partially amorphous; D-(S)-lenalidomide |
| Form 3 | stoichiometric dihydrate; crystalline; D-(S)-lenalidomide |
| Amorphous form | amorphous; D-(S)-lenalidomide |

The metastable hydrate and partially crystalline/amorphous characteristics of Form 2 may be used to characterize Form 2. The stoichiometric dihydrate composition characteristic of Form 3 may be used to characterize Form 3. The amorphous characteristic of the remaining solid form disclosed herein may be used to characterize it. These structural characteristics differentiate and thus may be used to characterize the forms. Crystalline and amorphous forms of compounds other than D-(S)-lenalidomide are not relevant because those compounds can be distinguished on chemical structure using, for example, solution-state analyses.

As used herein, the term "Form 1 of D-(S)-lenalidomide" means that solid form of the compound of Formula I which is anhydrous and crystalline. The term "Form 2 of D-(S)-lenalidomide" means that solid form of the compound of Formula I which is a crystalline metastable hydrate. The term "Form 3 of D-(S)-lenalidomide" means that solid form of the compound of Formula I which is a crystalline dihydrate. The term "amorphous form" means that solid form of the compound of Formula I which is amorphous.

The solid-state analytical data disclosed herein may further be used to characterize the solid forms. For example, FIG. 1 is the powder-x-ray diffraction pattern of a sample of Form 1 of D-(S)-lenalidomide. That pattern contains several peaks which may be used to further characterize the form. For example, in one embodiment, the peak at about 8.0°2Θ may be used to further characterize that solid form. In further embodiments, any one or more of the peaks at about 8.0, 9.4, 17.3, 19.3, or 17.5°2Θ may be used to characterize the form. In yet a further embodiment, any one or more (including five or more or ten or more) of the peaks at about 8.0, 9.4, 11.7, 16.1, 17.3, 17.5, 18.7, 19.3, 22.5, 24.1, 25.4, 27.0 and 29.7°2Θ may be used to further characterize that solid form. In still a further embodiment, a diffraction pattern substantially the same as that found in FIG. 1 may also be used to further characterize Form 1 of D-(S)-lenalidomide.

Figure 2:
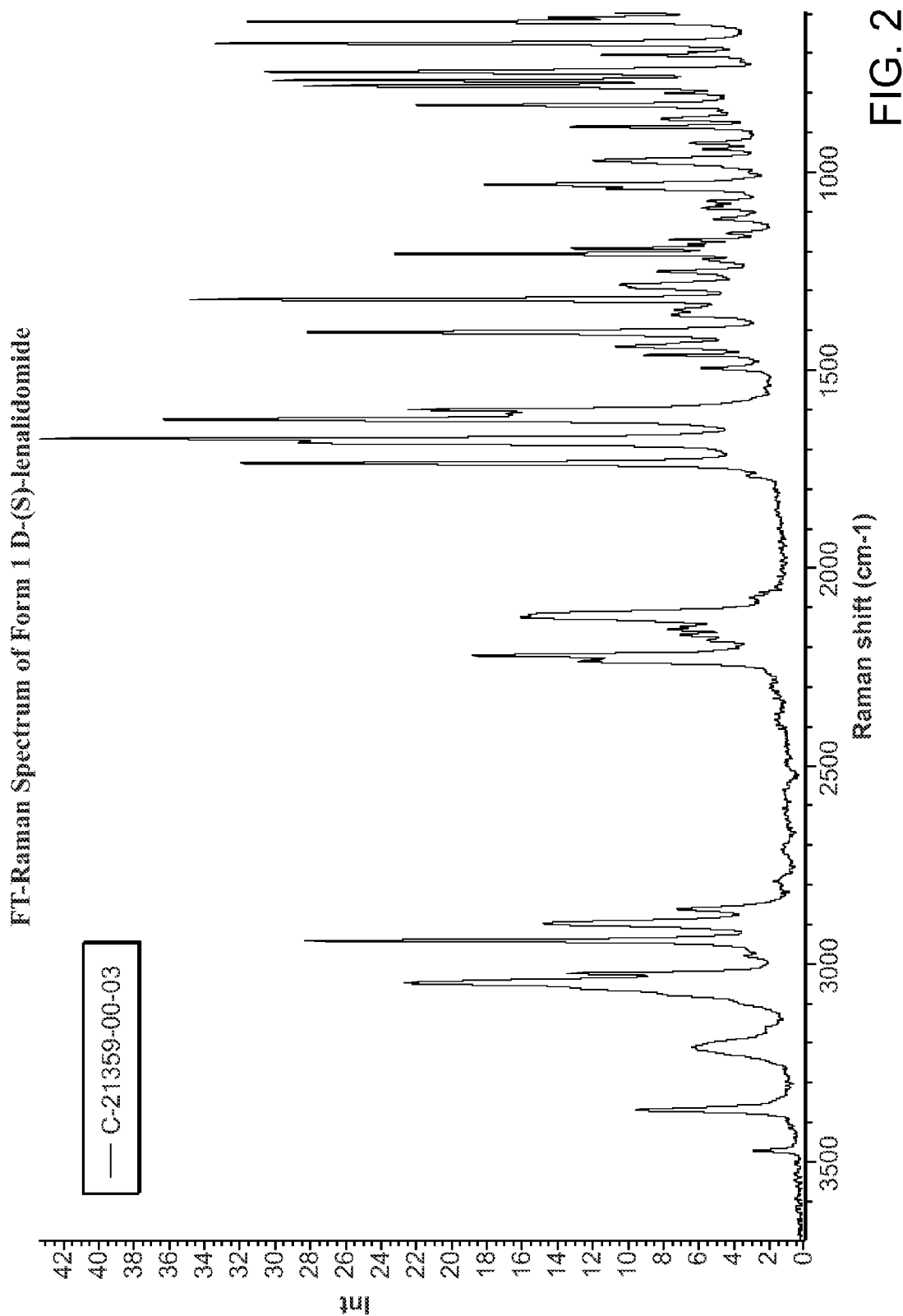
FIG. 2. is an FT-Raman spectrum of Form 1 of D-(S)-lenalidomide.

Other analytical techniques, either alone, or in combination with x-ray powder diffraction may be used to characterize Form 1 of D-(S)-lenalidomide. For example, peaks selected from the Raman spectrum of a sample of Form 1 in FIG. 2 may further be used to characterize Form 1 of D-(S)-lenalidomide with or without the one or more PXRD peaks set forth herein and/or the other solid-state data herein. For example, in one embodiment, Form 1 of D-(S)-lenalidomide may further be characterized by a Raman peak at about 1735 $cm^{-1}$ with or without the one or more PXRD peaks set forth herein and/or the other solid-state data set forth herein. In another embodiment, Form 1 of D-(S)-lenalidomide may be further characterized by a peak at about 1735 $cm^{-1}$ and/or a peak at about 1673 $cm^{-1}$ with or without the one or more PXRD peaks set forth herein and/or the other solid-state data set forth herein. In still a further embodiment, Form 1 of D-(S)-lenalidomide may be further characterized by a Raman spectrum having substantially the same pattern as that found in FIG. 2 alone or in connection with the powder x-ray diffraction data or other solid-state data herein.

Figure 3:
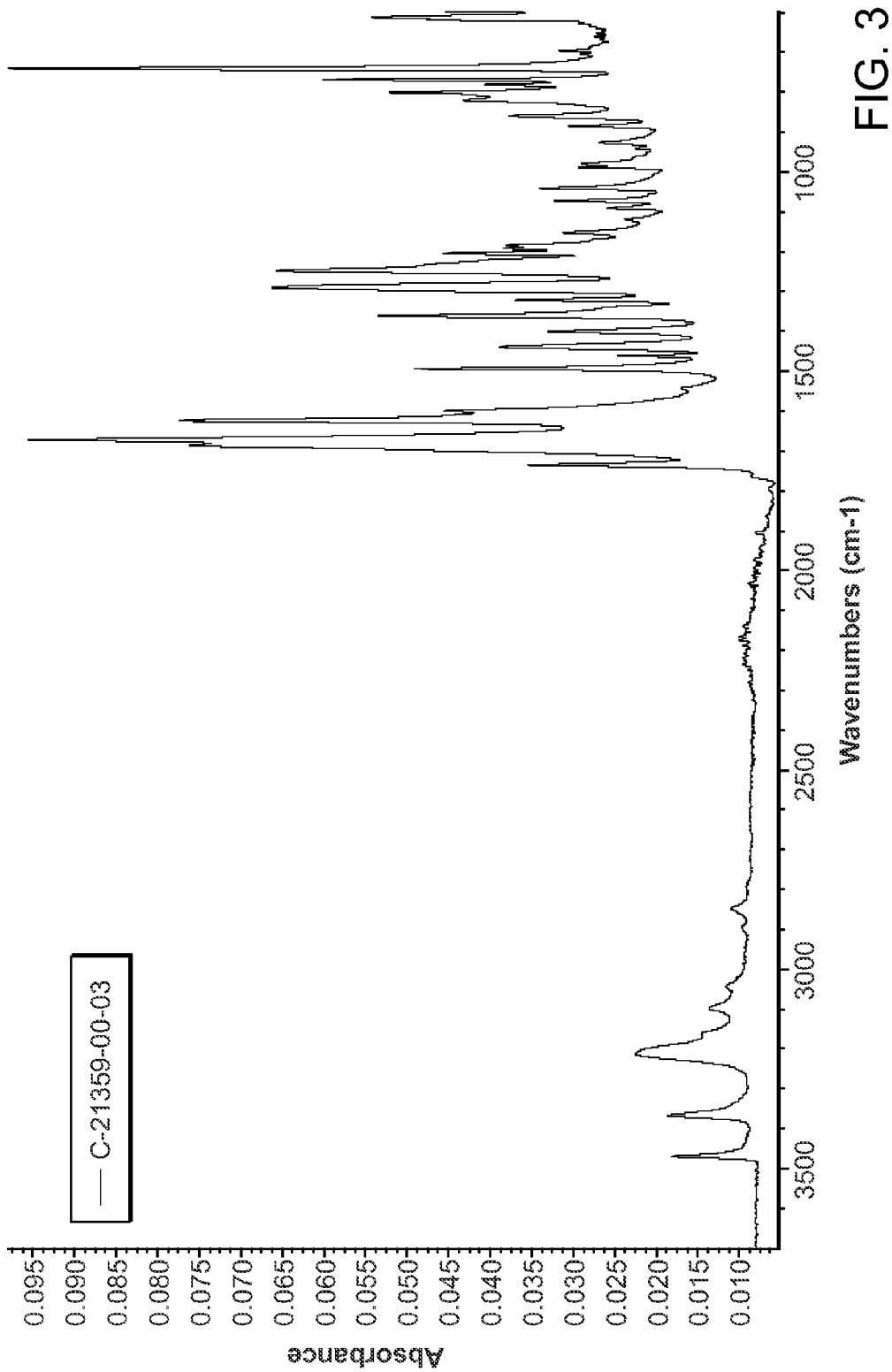
FIG. 3 is an FT-IR spectrum of Form 1 of D-(S)-lenalidomide.

An analytical technique related to Raman is infrared (IR) spectroscopy. The FT-IR spectrum of a sample of Form 1 of D-(S)-lenalidomide can be found at FIG. 3. Peaks from the FT-IR spectrum of a sample of Form 1 in FIG. 3 may further be used to characterize Form 1 of D-(S)-lenalidomide with or without the one or more PXRD peaks set forth herein and/or one or more Raman peaks set forth herein and/or the other solid-state data herein. For example, in one embodiment, Form 1 of D-(S)-lenalidomide may further be characterized by an FT-IR spectral peak at about 1735 $cm^{-1}$ with or without one or more PXRD peaks set forth herein and/or one or more Raman peaks set forth herein and/or or the other solid-state data set forth herein. In another embodiment, Form 1 of D-(S)-lenalidomide may be further characterized by a peak at about 1735 $cm^{-1}$ and/or a peak at about 1289 $cm^{-1}$ with or without one or more PXRD peaks set forth herein and/or one or more Raman peaks set forth herein and/or or the other solid-state data set forth herein. In still a further embodiment, Form 1 of D-(S)-lenalidomide may be further characterized by an FT-IR spectrum having substantially the same pattern as that found in FIG. 3 alone or in connection with the powder x-ray diffraction data and/or the Raman data and/or other solid-state data herein.

Another analytical technique which may be used alone or together with the other solid-state analytical data herein is melting point determination. For example, Form 1 of D-(S)-lenalidomide melts at about 250° C. as measured by DSC in FIG. 4.

The solubility estimates of Form 1 determined in multiple solvents is disclosed in Example 13 and Table 2.

In one embodiment, Form 1 is substantially free of other forms of D-(S)-lenalidomide. Here "other forms" includes other crystalline forms, such as Forms 2 and 3 (disclosed herein), as well as D-(S)-lenalidomide in amorphous form. In this aspect, the term "substantially free of other forms" means that the sum of the amounts of other forms is less than 50%, more preferably equal to or less than 20%, more preferably equal to or less than 10%, more preferably equal to or less than 5%, more preferably equal to or less than 1%, or more preferably equal to or less than 0.1%, of the amount of Form 1.

Figure 8:
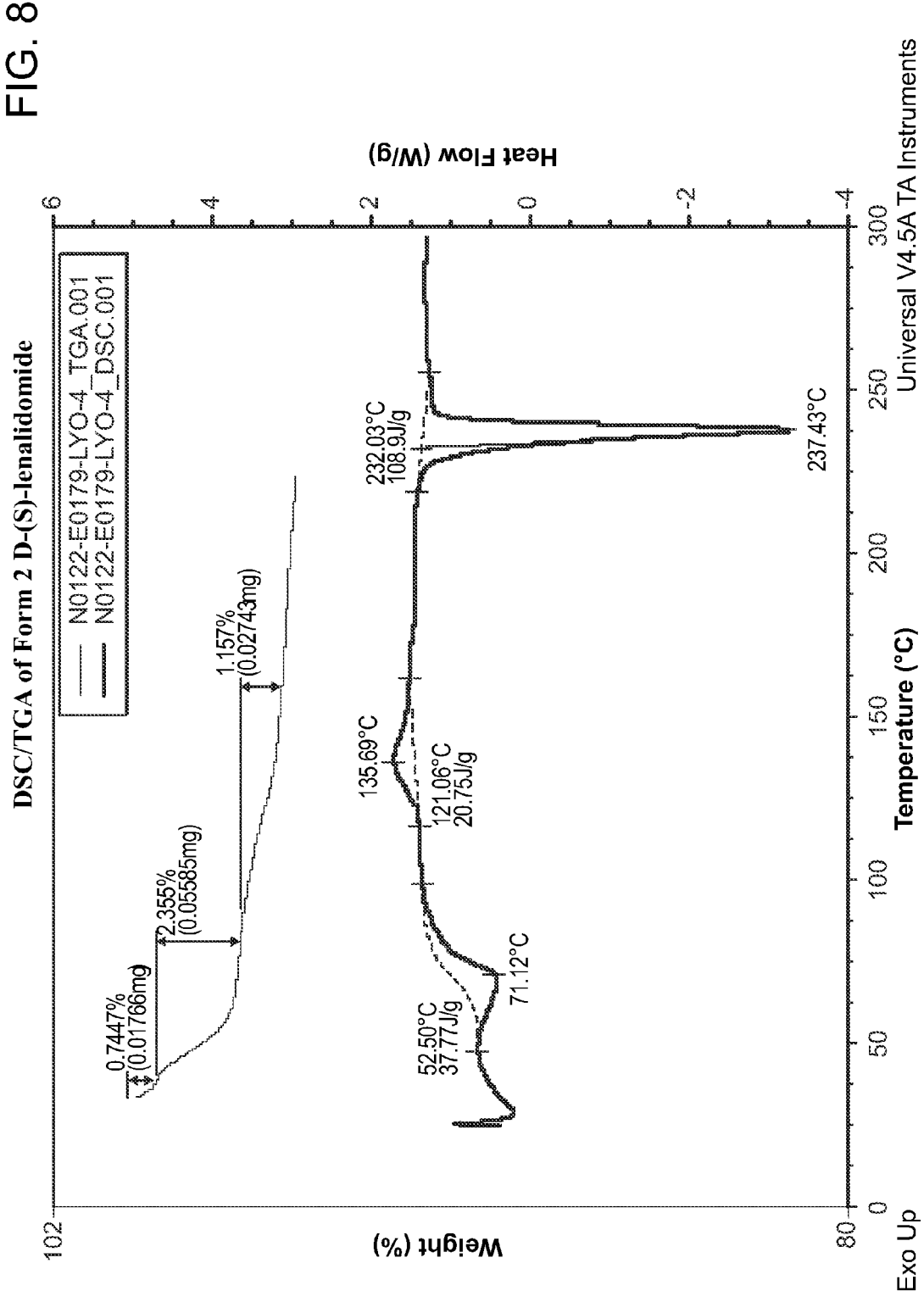
FIG. 8 is plot showing DSC and TGA data for Form 2 of D-(S)-lenalidomide.

Form 2 of D-(S)-lenalidomide was found to be a metastable hydrate possessing both crystalline and amorphous character. Form 2 converted to Forms 1 and 3 under room temperature storage conditions whereas Form 3 formed when Form 2 was stirred in cold water after twelve hours at 5° C. In a DSC experiment, Form 2 dehydrated at about 52.5° C. Upon continued heating, a crystallization event was found at 121° C. (FIG. 8).

Figure 6:
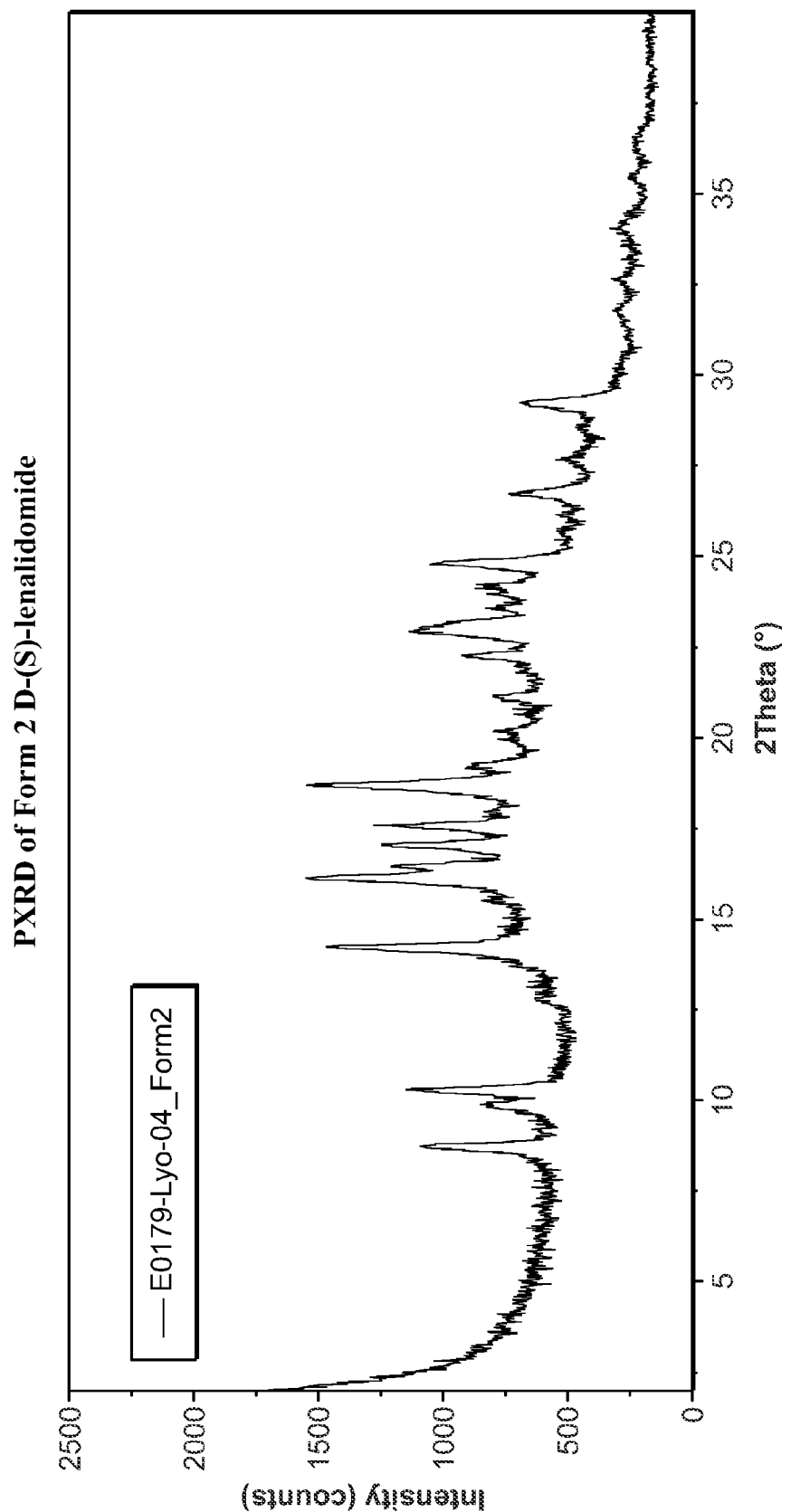
FIG. 6 is a powder x-ray diffraction ("PXRD") pattern of Form 2 of D-(S)-lenalidomide.

In addition to its characteristics, Form 2 may also be further characterized by the same kinds of analytical techniques used to further characterize Form 1 such as PXRD, Raman and DSC. For example, turning to FIG. 6, which is the PXRD pattern of Form 2 of (D)-(S) Lenalidomide, one or more of the peaks therein may be used to further characterize Form 2 of (D)-(S) Lenalidomide. For example, in one embodiment, the peak at about 8.8°2Θ may be used to further characterize Form 2 of D-(S)-lenalidomide. In further embodiments, for example, one or more (including four or more) of the peaks at about 8.8, 10.3, 14.3, 16.2, and 24.8° 2Θ may be used to further characterize Form 2 of D-(S)-lenalidomide. In further embodiments, for example, one or more (including five or more) of the peaks at about 8.8, 10.3, 14.3, 16.2, 18.7, and 24.8°2Θ may be used to further characterize Form 2 of D-(S)-lenalidomide. In further embodiments, for example, one or more of the peaks at about 8.8, 10.3, 14.3, 16.2, 17.0, 18.7, 21.1, 22.3, 24.8 and 26.7°2Θ may be used to further characterize Form 2 of D-(S)-lenalidomide. In still a further embodiment, a diffraction pattern substantially the same as that found in FIG. 6 may also be used to further characterize Form 2 of D-(S)-lenalidomide.

Figure 7:
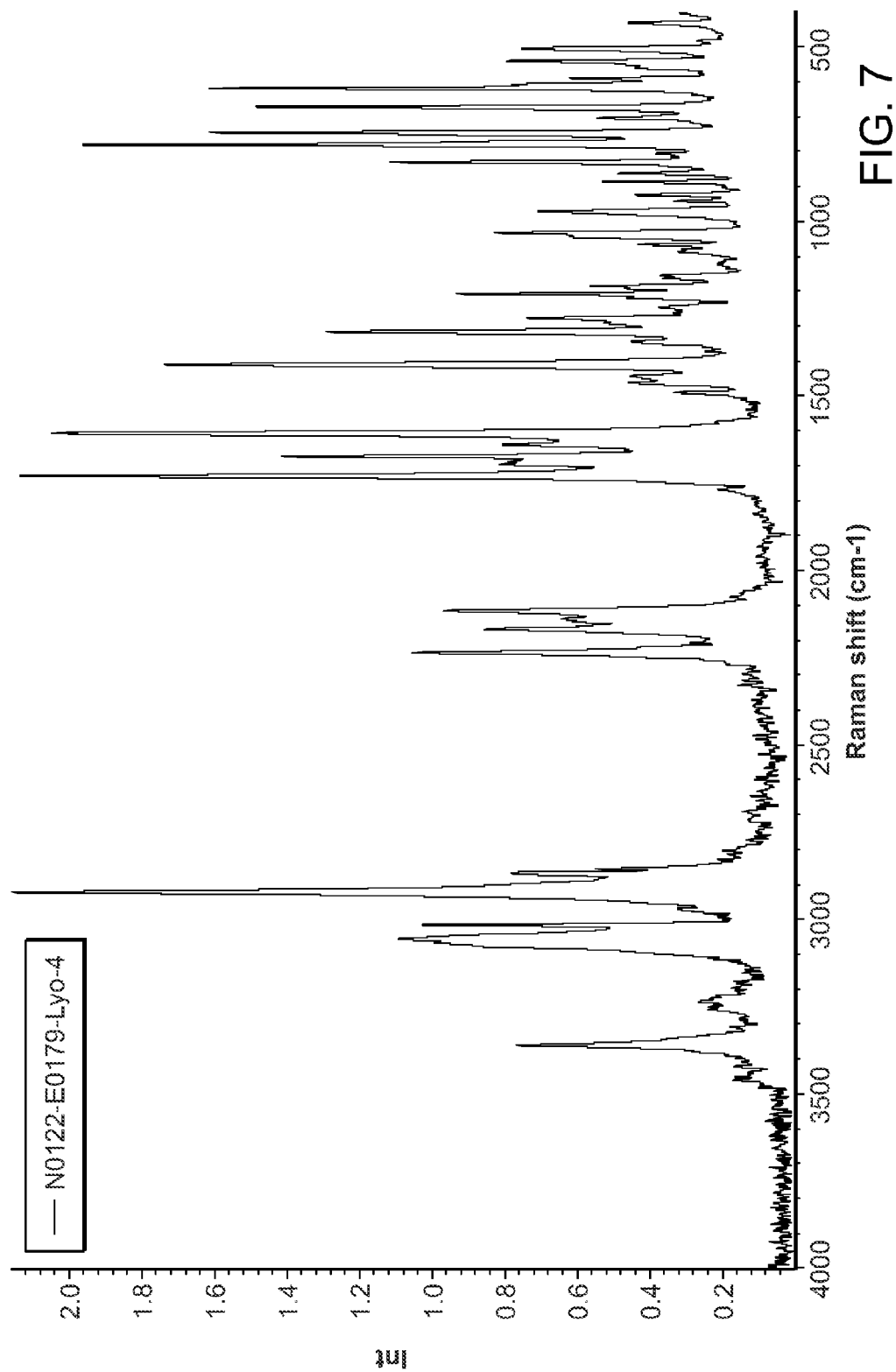
FIG. 7 is an FT-Raman spectrum of Form 2 of D-(S)-lenalidomide.

Other analytical techniques, either alone, or in combination with x-ray powder diffraction may be used to characterize Form 2 of D-(S)-lenalidomide. For example, peaks selected from the Raman spectrum of a sample of Form 2 of D-(S)-lenalidomide in FIG. 7 may further be used to characterize Form 2 of D-(S)-lenalidomide with or without the PXRD peaks set forth herein or the other solid-state data herein. For example, in one embodiment, Form 2 of D-(S)-lenalidomide may further be characterized by a Raman peak at about 2922 $cm^{-1}$ with or without the one or more PXRD peaks set forth herein and/or the other solid-state data set forth herein. In another embodiment, Form 2 of D-(S)-lenalidomide may be further characterized by a peak at about 2922 $cm^{-1}$ and/or a peak at about 1729 $cm^{-1}$ with or without the one or more PXRD peaks set forth herein and/or the other solid-state data set forth herein. In still a further embodiment, Form 2 of D-(S)-lenalidomide may be further characterized by a Raman spectrum having substantially the same pattern as that found in FIG. 7 alone or in connection with the powder x-ray diffraction data or other solid-state data herein.

In one embodiment, Form 2 is substantially free of other forms of D-(S)-lenalidomide. Here "other forms" includes other crystalline forms, such as Forms 1 and 3 (disclosed herein), as well as D-(S)-lenalidomide in amorphous form. In this aspect, the term "substantially free of other forms" means that the sum of the amounts of other forms is less than 50%, more preferably equal to or less than 20%, more preferably equal to or less than 10%, more preferably equal to or less than 5%, more preferably equal to or less than 1%, or more preferably equal to or less than 0.1%, of the amount of Form 2.

Figure 11:
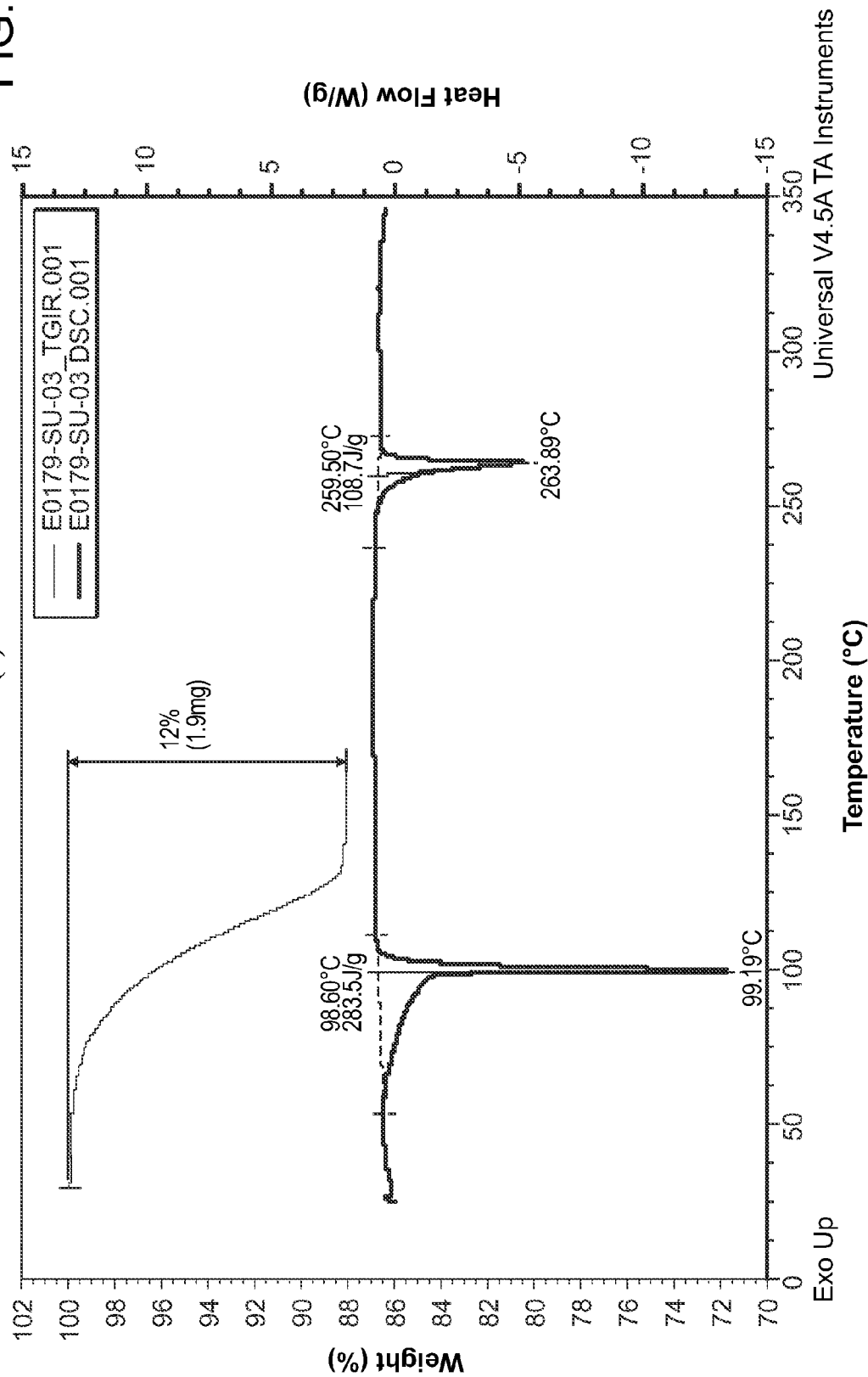
FIG. 11 is a plot showing DSC and TGA data for Form 3 of D-(S)-lenalidomide.
Figure 12:
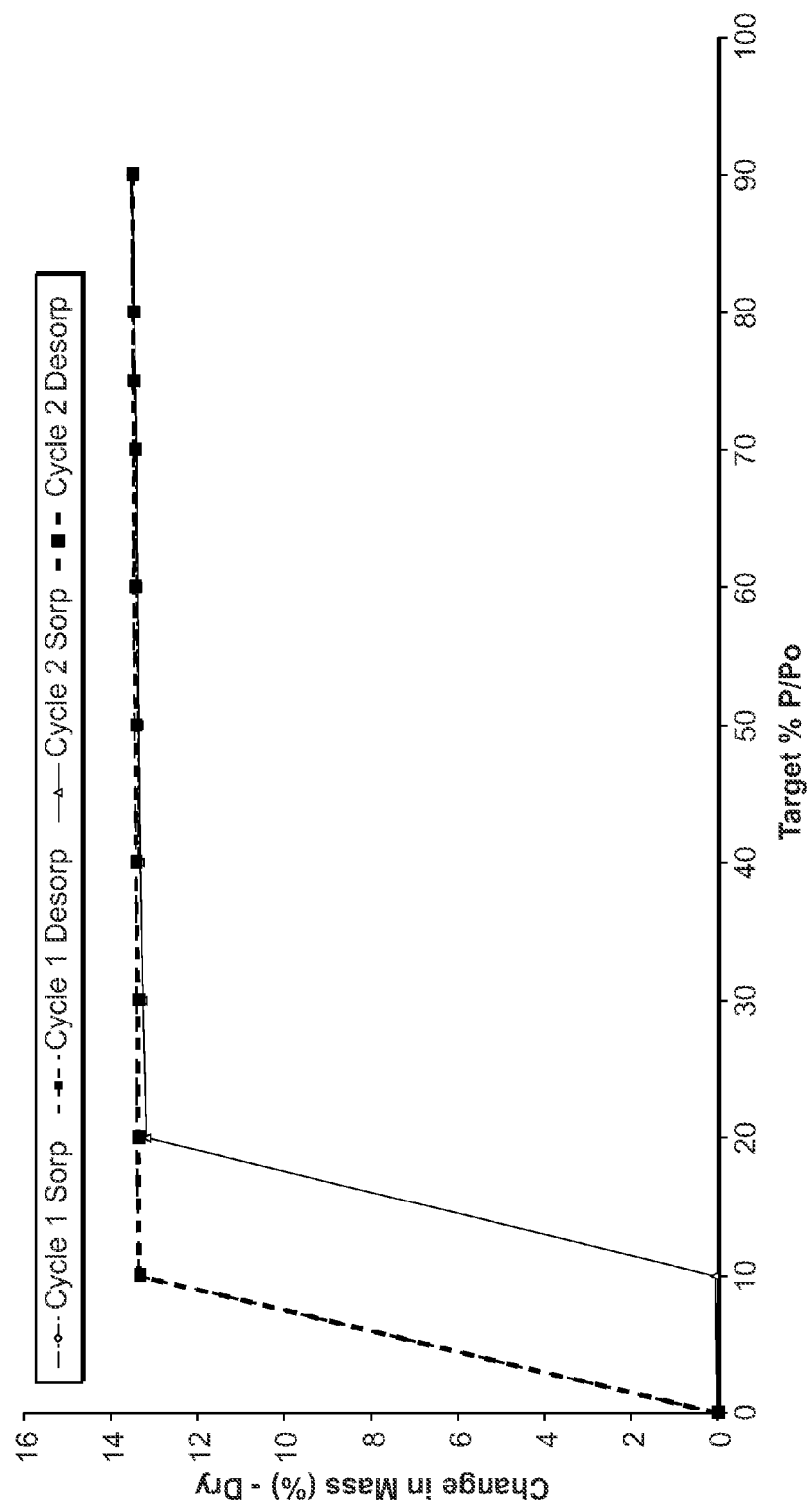
FIG. 12 is a DVS plot of Form 3 of D-(S) of Lenalidomide.

Form 3 of D-(S)-lenalidomide was determined to be a crystalline dihydrate of the compound of Formula I and can be characterized accordingly. DVS analysis of Form 3 of D-(S)-lenalidomide at room temperature indicated no weight change between 20-90% relative humidity (FIG. 12). Below 20% relative humidity, Form 3 of D-(S)-lenalidomide was shown to dehydrate and re-hydrate with a relatively small hysteresis. PXRD analysis of the residual solid, equilibrated at 0% RH for four hours indicated no change in solid form when compared to the reference PXRD pattern. Form 3 of D-(S)-lenalidomide is physically stable when stored in a closed vial for at least 3 weeks. A partial conversion to Form 1 of D-(S)-lenalidomide was observed when stored at 40° C./75% relative humidity for 6 days, as determined by PXRD. In a DSC experiment, Form 3 dehydrated at about 98.6° C. and subsequently melted at about 259.5° C. (FIG. 11).

Figure 9:
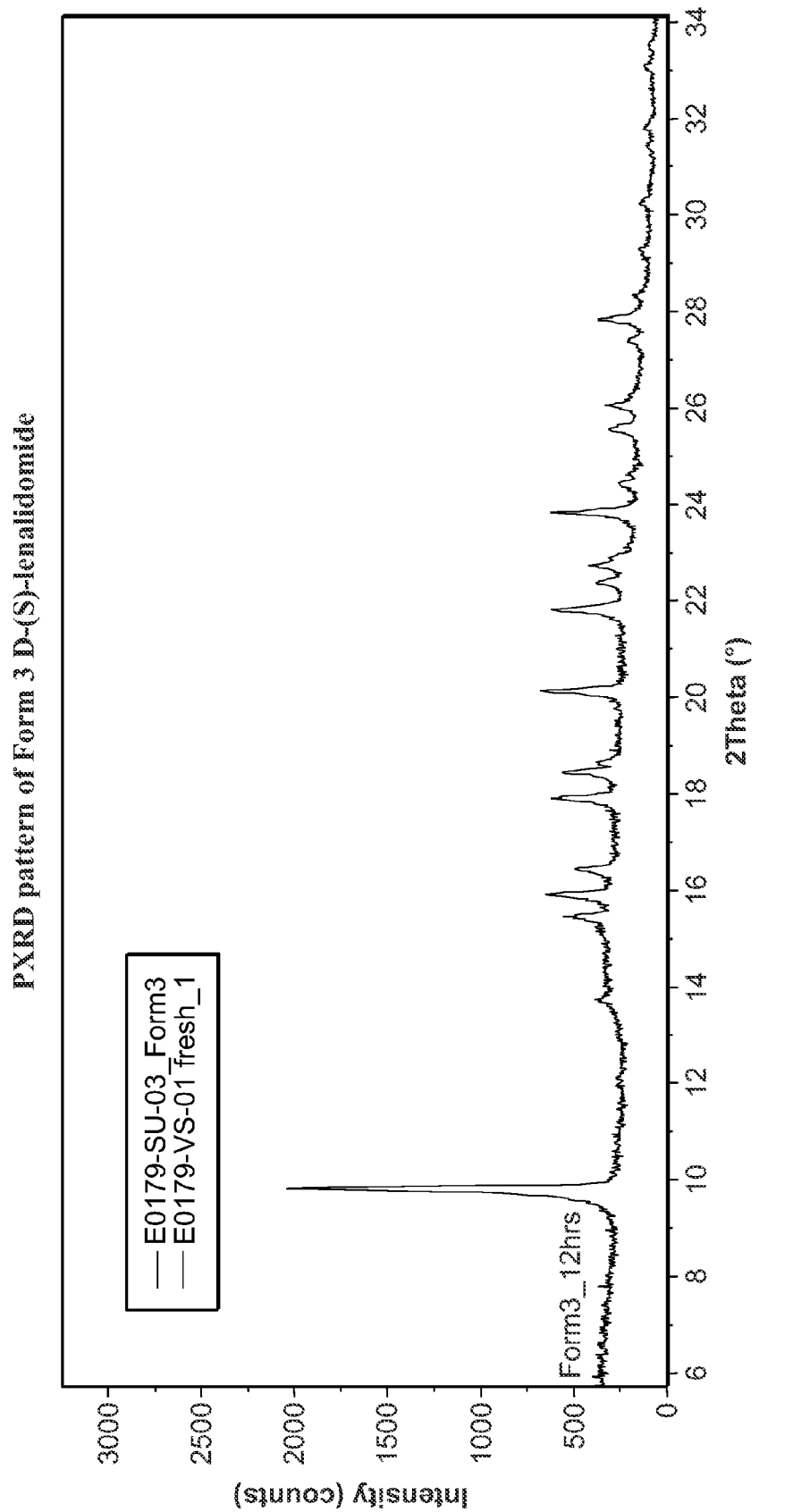
FIG. 9 is a powder x-ray diffraction ("PXRD") pattern of Form 3 of D-(S)-Lenalidomide.

In addition to its characteristics of being a crystalline dihydrate of the compound of Formula I, Form 3 may also be further characterized by the same kinds of analytical techniques used to further characterize the other solid forms of the compound of Formula I such as PXRD, Raman and DSC. For example, turning to FIG. 9, which is the PXRD pattern of Form 3 of D-(S)-lenalidomide, one or more of the peaks therein may be used to further characterize Form 3 of D-(S)-lenalidomide. For example, in one embodiment, the peak at about 17.9°2Θ may be used to further characterize Form 3 of D-(S)-lenalidomide. In further embodiments, for example, one or more (including four or more) of the peaks at about 9.8, 17.9, 20.1, 21.8, and 23.8°2Θ may be used to further characterize Form 3 of D-(S)-lenalidomide. In further embodiments, for example, one or more (including five or more) of the peaks at about 9.8, 17.9, 18.5, 20.1, 21.8, and 23.8°2Θ may be used to further characterize Form 3 of D-(S)-lenalidomide. In further embodiments, for example, one or more of the peaks at about 9.8, 13.7, 17.9, 18.5, 20.1, 21.8, 22.7, 23.8, 26.1 and 27.8°2Θ may be used to further characterize Form 3 of D-(S)-lenalidomide. In still a further embodiment, a diffraction pattern substantially the same as that found in FIG. 9 may also be used to further characterize Form 3 of D-(S)-lenalidomide.

Figure 10:
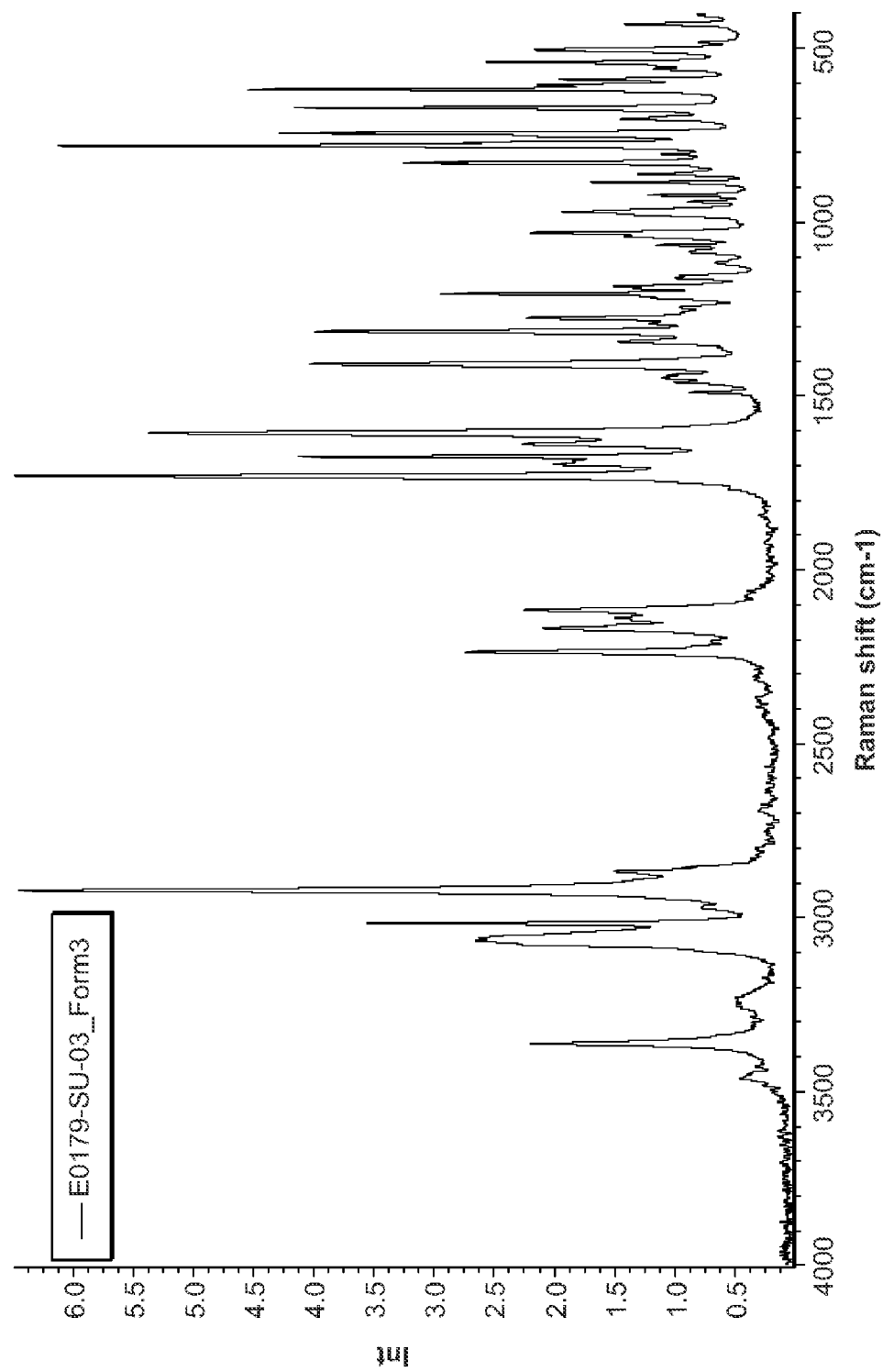
FIG. 10 is an FT-Raman spectrum of Form 3 of D-(S)-lenalidomide.

Other analytical techniques, either alone, or in combination with x-ray powder diffraction may be used to characterize Form 3 of D-(S)-lenalidomide. For example, peaks selected from the Raman spectrum of a sample of Form 3 of D-(S)-lenalidomide in FIG. 10 may further be used to characterize Form 3 of D-(S)-lenalidomide with or without the PXRD data set forth above or the other solid-state data herein. For example, in one embodiment, Form 3 of D-(S)-lenalidomide may further be characterized by a Raman peak at about 2237 $cm^{-1}$ with or without the one or more PXRD peaks set forth herein and/or the other solid-state data set forth herein. In another embodiment, Form 3 of D-(S)-lenalidomide may be further characterized by a peak at about 2237 $cm^{-1}$ and/or a peak at about 1606 $cm^{-1}$ with or without the one or more PXRD peaks set forth herein and/or the other solid-state data set forth herein. In still a further embodiment, Form 3 of D-(S)-lenalidomide may be further characterized by a Raman spectrum having substantially the same pattern as that found in FIG. 10 alone or in connection with the powder x-ray diffraction data or other solid-state data herein.

In one embodiment, Form 3 is substantially free of other forms of D-(S)-lenalidomide. Here "other forms" includes other crystalline forms, such as Forms 1 and 2 (disclosed herein), as well as D-(S)-lenalidomide in amorphous form. In this aspect, the term "substantially free of other forms"

means that the sum of the amounts of other forms is less than 50%, more preferably equal to or less than 20%, more preferably equal to or less than 10%, more preferably equal to or less than 5%, more preferably equal to or less than 1%, or more preferably equal to or less than 0.1%, of the amount of Form 3.

Figure 13A:
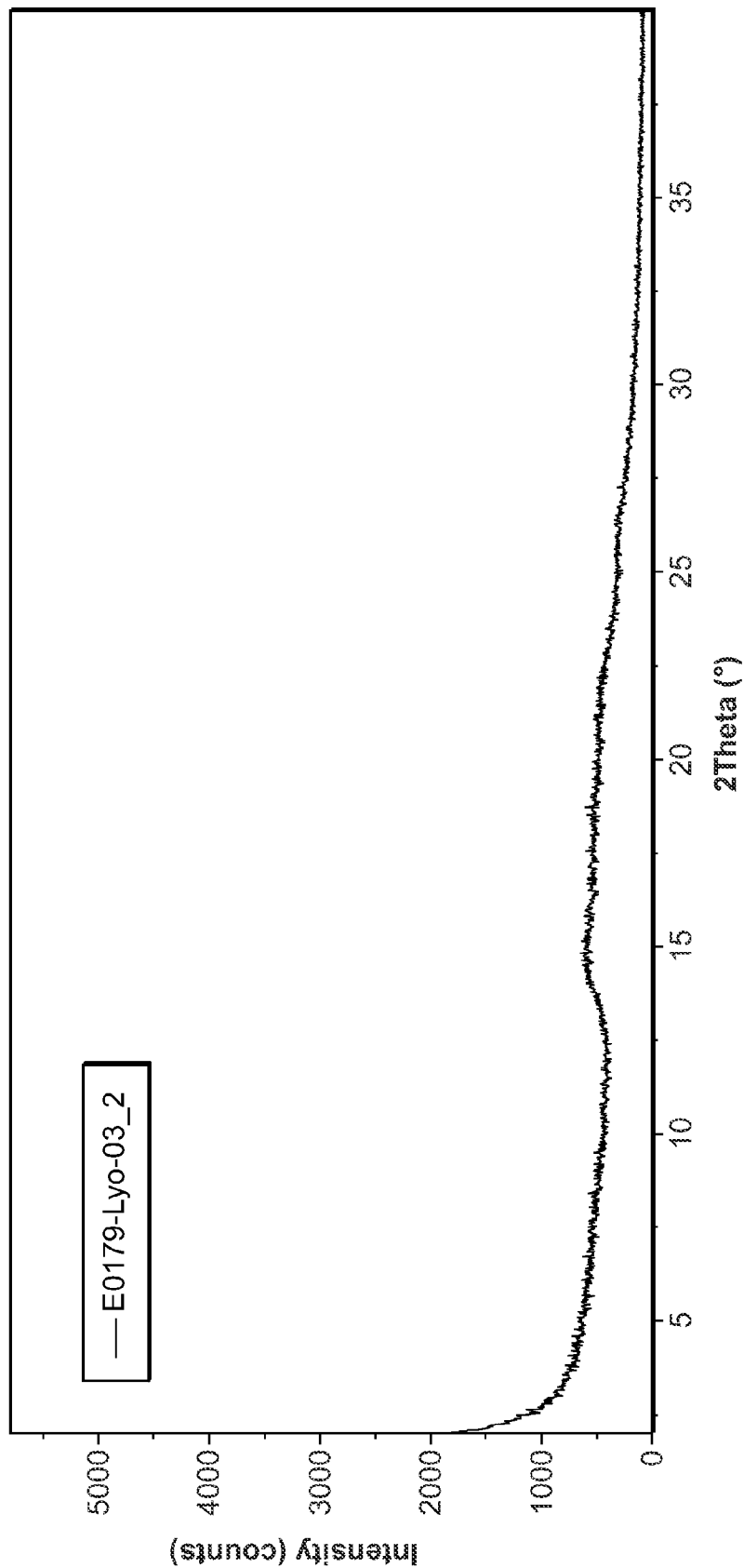
FIG. 13A is a powder x-ray diffraction ("PXRD") pattern of amorphous D-(S)-lenalidomide prepared by lyophilization.
Figure 13B:
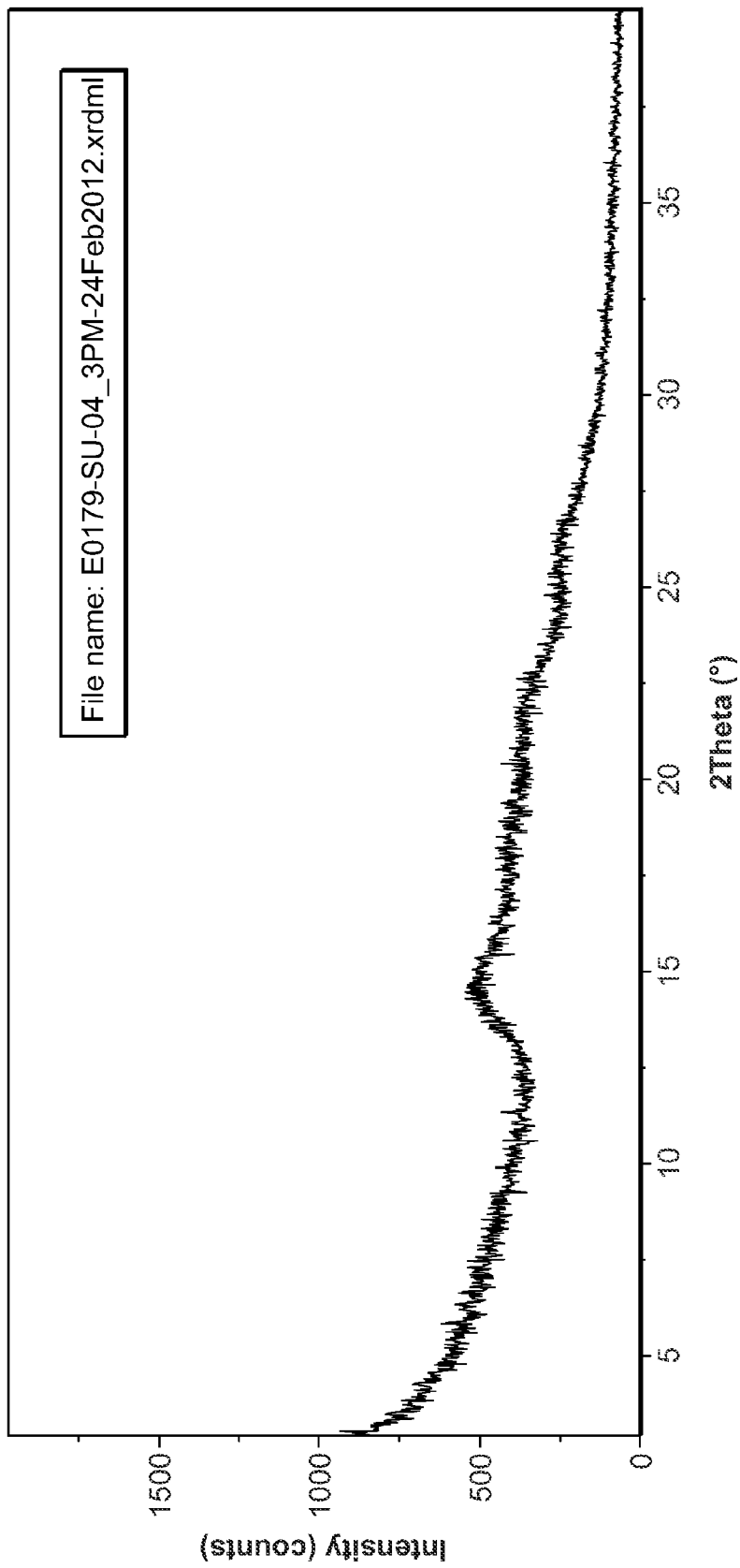
FIG. 13B is a powder x-ray diffraction ("PXRD") pattern of amorphous D-(S)-lenalidomide prepared by evaporation.
Figure 14:
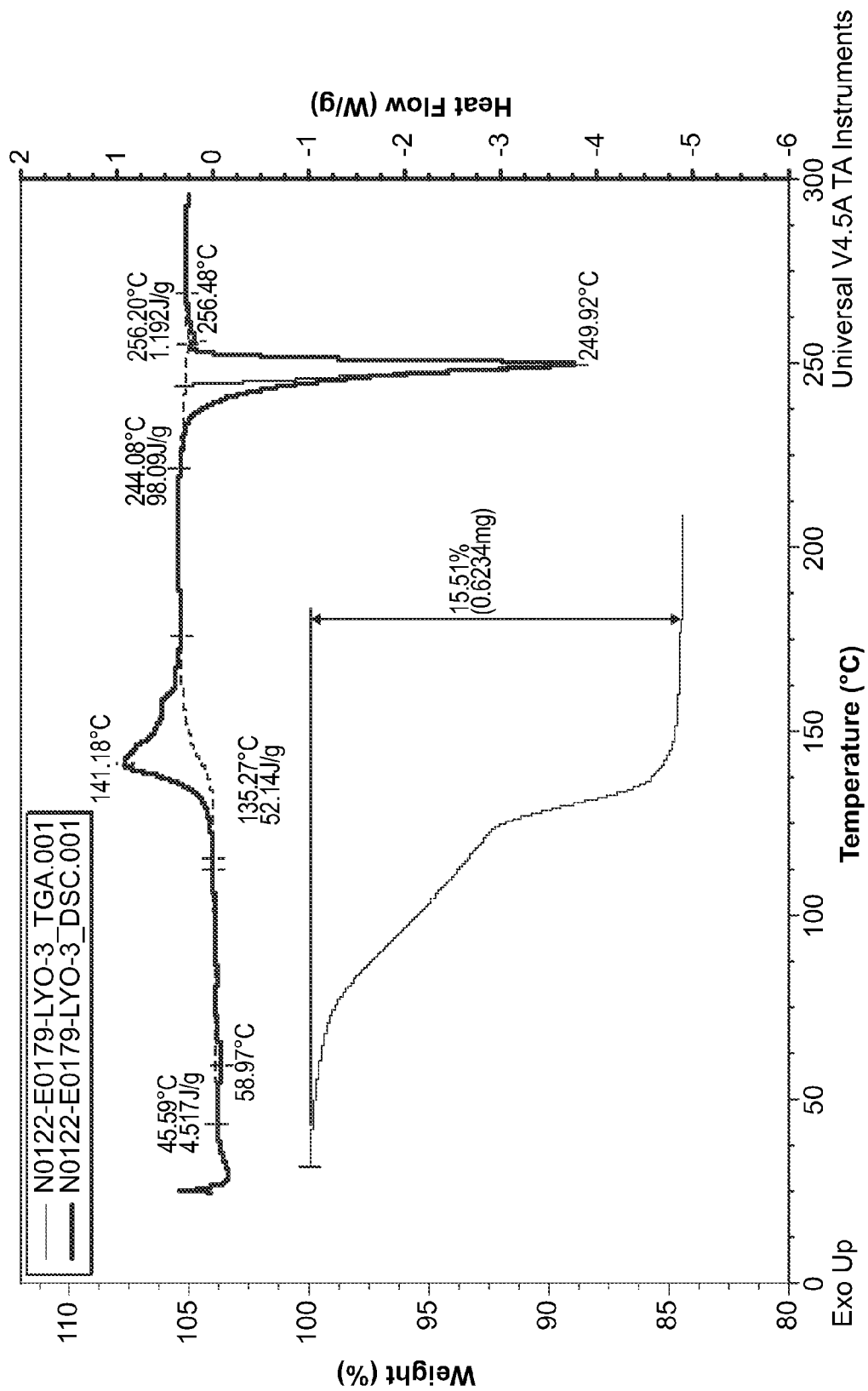
FIG. 14 is a plot showing DSC and TGA data for amorphous D-(S)-lenalidomide.

The remaining solid form of D-(S)-lenalidomide disclosed herein was found to be amorphous as indicated by FIGS. 13A and 13B and can be characterized accordingly. This amorphous form was prepared in one case by lyophilization and by rapid evaporation from solution in another. The two different routes of preparing this form lead to amorphous material with different physical properties. The material made by the lyophilization route had a very low bulk density, but was found to be extremely pure (>99.9%) whereas the material made from a solution in an organic solvent by rapid evaporation produced a glassy/tacky material. By DSC, upon heating, the amorphous form undergoes a crystallization event at about 135° C. (FIG. 14).

Lyophilization may be performed in a solvent system with one or more solvents. In one embodiment, the solvent system contains one or more organic solvents. Examples of organic solvents include acetonitrile and 1,4-dioxane. A solid form of D-(S)-lenalidomide is suspended or dissolved in solvent system. In another embodiment, the lyophilization takes place from a frozen mixture of solution of the solvent system and D-(S)-lenalidomide.

Formation of the amorphous form by evaporation occurs, in one embodiment, from a solvent solution containing D-(S)-lenalidomide. In one embodiment, the solvent is methanol and evaporation occurs by rotary evaporation (herein also referred to as rotovapping).

The amorphous form may also be further characterized by the same kinds of analytical techniques used to further characterize the other solid forms of the compound of Formula I such as PXRD, and DSC. For example, turning to FIGS. 13A and 13B, which is the PXRD pattern of amorphous D-(S)-lenalidomide, a diffraction pattern substantially the same as that found in either of the patterns of FIG. 13A or 13B may also be used to further characterize amorphous D-(S)-lenalidomide.

In one embodiment, the amorphous form is substantially free of other forms of D-(S)-lenalidomide. Here "other forms" includes crystalline forms, such as Forms 1, 2 and 3 (disclosed herein). In this aspect, the term "substantially free of other forms" means that the sum of the amounts of other forms is less than 50%, more preferably equal to or less than 20%, more preferably equal to or less than 10%, more preferably equal to or less than 5%, more preferably equal to or less than 1%, or more preferably equal to or less than 0.1%, of the amount of amorphous form.

The invention also provides pharmaceutical compositions comprising an effective amount of a compound of Formula I (e.g., including any of the formulae herein), or a pharmaceutically acceptable salt thereof; and an acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington: The Science and Practice of Pharmacy, Lippincott Williams and Wilkins, Baltimore, Md. (20th ed. 2000).

Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

According to another embodiment, the invention provides a method of treating a disease that is beneficially treated by lenalidomide in a patient in need thereof, comprising the step of administering to the patient an effective amount of a compound or a composition of this invention. Such diseases are well known in the art and are disclosed in U.S. Pat. No. 5,635,517, as well as in PCT patent publications WO2005097125, WO2005055929, WO2004041190, WO2006060507, WO2006058008, WO2006053160, WO2005044178, WO2004100953, WO2006089150, WO2006036892, WO2006018182, WO2005082415, WO2005048942, WO2005042558, WO2005035714 and WO2005027842; and in United States Patent publications US2005100529, US2006030594, US2005143344 and US2006079461.

In one preferred embodiment, the disease or condition is selected from myelodysplastic syndromes, multiple myeloma, Non-Hodgkins lymphoma; papillary and follicular thyroid carcinoma; prostate cancer; chronic lymphocytic leukemia, amyloidosis, complex regional pain syndrome Type I, malignant melanoma, radiculopathy, myelofibrosis, glioblastoma, gliosarcoma, malignant gliomas, myelogenous leukemia, refractory plasma cell neoplasm, chronic myelomonocytic leukemia, follicular lymphoma, ciliary body and chronic melanoma, iris melanoma, recurrent interocular melanoma, extraocular extension melanoma, solid tumors, T-cell lymphoma, erythroid lymphoma, monoblastic and monocytic leukemia; myeloid leukemia, brain tumor, meningioma, spinal cord tumors, thyroid cancers, mantle cell lymphoma, non-small cell lung cancer, ovarian cancer, prostate cancer, renal cell cancer, myelofibrosis, Burkitt's lymphoma, Hodgkin's lymphoma, large cell lymphoma, or Waldenstrom's macroglobulinemia.

In another embodiment, the disease is selected from myelodysplastic syndromes or multiple myeloma.

Identifying a patient in need of such treatment can be in the judgment of a patient or a health care professional and can be subjective (e.g. opinion) or objective (e.g. measurable by a test or diagnostic method).

Another aspect of the invention is a compound of Formula I for use in the treatment or prevention in a patient of a disease, disorder or symptom thereof delineated herein.

EXAMPLES

Instrumentation

FT-Raman Spectroscopy.

Fourier-Transform (FT) Raman spectra were collected with a Nicolet NXR9650 or NXR 960 spectrometer (Thermo Electron) equipped with 1064 nm Nd:YVO$_4$ excitation laser, InGaAs and liquid-N$_2$ cooled Ge detectors, and a Micro-Stage. All spectra were acquired at 4 cm$^{-1}$ resolution, 64-128 scans, using Happ-Genzel apodization function and 2-level zero-filling.

FT-IR Spectroscopy.

FT-IR spectra were collected with a Nicolet 6700 spectrometer (Thermo Electron) equipped with a DTGS detector and a SensiIR DuroScope DATR. All spectra were acquired at 4 cm$^{-1}$ resolution, 64 scans, using Happ-Genzel apodization function and 2-level zero-filling.

Polarized-Light Microscopy (PLM).

Polarized light photomicrographs were collected using Olympus BX60 polarized-light microscope equipped with Olympus DP70 camera.

Powder X-Ray Diffraction (PXRD).

PXRD diffractograms were acquired using PANalytical X'Pert Pro diffractometer on Si zero-background wafers. All diffractograms were collected using a monochromatic Cu Kα (45 kV/40 mA) radiation and a step size of 0.02° 2θ.

Differential Scanning Calorimetry (DSC).

DSC was conducted with a TA Instruments Q100 differential scanning calorimeter equipped with an autosampler and a refrigerated cooling system under 40 mL/min N$_2$ purge. DSC thermograms were obtained at 15° C./min in crimped Al pans.

Thermogravimetric Analysis (TGA).

TGA thermograms were obtained with a TA Instruments Q500 thermogravimetric analyzer under 40 mL/min N$_2$ purge at 15° C./min in Pt or Al pans.

Thermogravimetric Analysis with IR Off-Gas Detection (TGA-IR).

TGA-IR was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min N$_2$ flow and heating rate of 15° C./min in Pt or Al pans. IR spectra were collected at 4 cm$^{-1}$ resolution and 32 scans at each time point.

Dynamic Vapor Sorption (DVS).

DVS experiments were conducted on a Surface Measurement Systems DVS-HT at 25° C. The instrument was operated in step mode and the relative humidity was increased in 10% RH increments from 40% RH to 90% RH, then decreased from 90% RH to 0% RH, then increased from 0% RH to 90% RH, then decreased from 90% RH to 0% RH. An extra step at 75% RH was included in each cycle. The mass equilibrium criterion was set at 0.005% change in mass over time (dm/dt) prior to each humidity level. A minimum step time of 10 minutes and a maximum step time of 240 minutes were specified.

High-Performance Liquid Chromatography (HPLC).

HPLC analyses were conducted with an HP1100 system equipped with a G1131 Quad pump, G1367A autosampler, and G1315B diode array detector. Column: Luna C18(2) (50×2.0 mm, 3 μm). Mobile phase: 100% vol. water (0.05% vol. TFA) to 95% acetonitrile (0.05% vol. TFA) over 8 min and 2 min re-equilibration. Flow rate: 1 mL/min. Detection: 254 nm.

Example 1a

Preparation of 3-amino-3,4,4,5,5-d$_5$-piperidine-2,6-dione (15)

Intermediate 15 was prepared as outlined in Scheme 1 and as described below.

Scheme 1: Synthetic Route to Intermediate 15

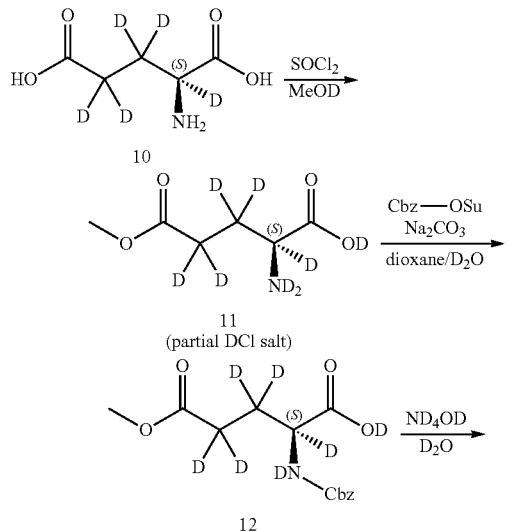

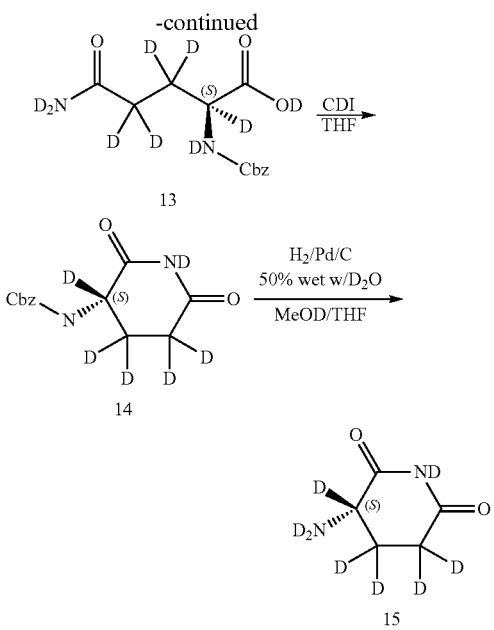

Step 1. (S)-2-Amino-2,3,3,4,4-$d_5$-5-methoxy-5-oxo-pentanoic acid (11)

Glutamic acid-d5, 10 (10.0 g, 65 mmol, 1.0 equiv, Cambridge Isotopes, 98 atom % D) was suspended in methanol-D (60 mL; Cambridge Isotopes, 99 atom % D) and spun on a rotary evaporator (rotovap) in a 40° C. water bath for 30 minutes and then was concentrated under reduced pressure. This process was repeated a second time. Methanol-D (120 mL; Cambridge Isotopes, 99 atom % D) was added to the resulting solid and the suspension was cooled in an ice bath. Thionyl chloride (6.2 mL, 85.5 mmol 1.3 equiv) was added dropwise resulting in a clear solution. The mixture was stirred cold for 1.5 hours then evaporated under reduced pressure using a cool bath to give a sticky white solid. Toluene (200 mL) was added to the residue and the mixture was evaporated. The material was dried in a vacuum oven at ambient temperature overnight to give 13.4 g of 11 (partial DCl salt) as an approximately 10:1 mixture of mono and di-esters.

Step 2. Compound 12

To a suspension of 11 (13.4 g, 65 mmol, assumes 100% yield in previous step, 1.0 equiv) and N-(benzyloxycarbonyloxy)succinimide (16.2 g, 65 mmol, 1.0 equiv) in dioxane (200 mL) and $D_2O$ (200 mL; Cambridge Isotopes, 99 atom % D) was added sodium carbonate (13.8 g, 130 mmol, 2.0 equiv) and the reaction mixture was stirred at room temperature under nitrogen overnight. The suspension was concentrated under reduced pressure to remove dioxane and the resulting aqueous solution was washed with ethyl acetate (100 mL, discarded). The aqueous phase was cooled to 0° C. and acidified to pH 2 by the dropwise addition of 35% DCl in $D_2O$ (Aldrich, 99 atom % D). The resulting milky solution was extracted with ethyl acetate (3×100 mL), the combined organic extracts were dried ($Na_2SO_4$) and concentrated under reduced pressure to give 23.0 g of 12 as a yellow oil. The crude product was purified by silica gel chromatography (300 g silica) eluting with 75:25 to 40:60 v/v heptanes:ethyl acetate to give 16.5 g (83% over 2 steps) of 12 as a clear oil which gradually solidified. The material had 2% H at the chiral center.

Step 3. Compound 13

Compound 12 (12.0 g, 40 mmol) was added to ammonium deuteroxide in deuterium oxide (200 mL, 25% solution; Cambridge Isotopes, 99 atom % D) and the mixture was stirred at room temperature overnight. The resulting mixture was washed with a small amount of ethyl acetate (50 mL), and the aqueous layer was cooled in an ice bath and acidified to pH 1 with DCl in $D_2O$ (35%; Aldrich, 99 atom % D). The aqueous layer was then extracted with ethyl acetate (3×100 mL). The combined organic layers were dried ($Na_2SO_4$) and concentrated. The residue was dissolved in THF, diluted with toluene and concentrated to afford 11.2 g (97%) of 13 as a white solid with 2-3% H at the chiral center.

Step 4. Compound 14

To a solution of 13 (9.5 g, 32.7 mmol, 1.0 equiv) in anhydrous tetrahydrofuran (300 mL) at room temperature under nitrogen was added 1,1'-carbonyldiimidazole (6.4 g, 39.3 mmol, 1.2 equiv) and the reaction mixture was stirred at room temperature for 20 minutes (a thick precipitate formed). The reaction mixture was heated at reflux for 8 hours (the precipitate slowly dissolved as the reaction reached reflux), then stirred at room temperature overnight. The reaction was concentrated under reduced pressure and the residue was partitioned between ethyl acetate (200 mL) and 1M DCl in $D_2O$ (200 mL, diluted with $D_2O$ from 35% DCl (Aldrich, 99 atom % D). The organic phase was separated, washed with 1M DCl in $D_2O$ (200 mL), dried ($Na_2SO_4$), and concentrated under reduced pressure to a colorless syrup. The crude product was adsorbed onto silica gel and purified by silica gel chromatography eluting with 75:25 to 50:50 v/v heptanes/ethyl acetate to give 6.4 g (74%) of 14 as a white solid.

$^1$H NMR of the product indicated 8% proton incorporation at the chiral center of the piperidine-2,6-dione ring. Chiral LC showed this material to be 94.5% ee for the second eluting peak. (Chiralcel OJ, 4.6×250 mm, 10 um, 100% ethanol, 0.20 mL/min for 45 minutes).

Note: This reaction was run at various scales resulting in slightly variable levels of racemization:

| Lot | SM Mass | Product Mass | % ee | % H |
|---|---|---|---|---|
| 1 | 4.0 g | 2.7 g | 92.9 | 8 |
| 2 | 8.0 g | 5.5 g | 94.9 | 7 |
| 3 | 12.0 g | 8.9 g | 89.9 | 7 |
| 4 | 9.0 g | 6.6 g | 94.9 | 7 |
| 5 | 9.5 g | 6.4 g | 94.5 | 8 |

Note:
All lots were combined giving a total of 30.1 g of 14.

Step 5. Compound 15

Compound 14 (10 g, 38 mmol) was dissolved in methanol-D (120 mL; Cambridge Isotopes, 99 atom % D). The mixture was allowed to stand for 30 minutes, then was concentrated under reduced pressure to give a white solid. After repeating this process once, a solution of 14 (from above) in methanol-D (80 mL; Cambridge Isotopes, 99 atom % D) and anhydrous tetrahydrofuran (80 mL) was added to 10% Pd/C (400 mg, 50% wet with $D_2O$) and the mixture was hydrogenated at 40 psi of $H_2$ for 5-6 hours. The reaction mixture was filtered through Celite, washing the Celite pad with THF, and the filtrate was concentrated under reduced pressure to give a quantitative recovery (5.2 g) of 15 as a light blue solid. The reaction was repeated once at this scale and once on a 7.5 g scale.

Note: 15 slowly oxidizes over time, becoming a darker blue. This intermediate should be prepared immediately prior to use. If storage is required, it should be stored under nitrogen.

Example 1b

Preparation of Form 1 D-(S)-lenalidomide

Form 1 D-(S)-lenalidomide was prepared as outlined in Scheme 2 and as described below.

Scheme 2: Synthetic Route to Form 1 D-(S)-lenalidomide (18a)

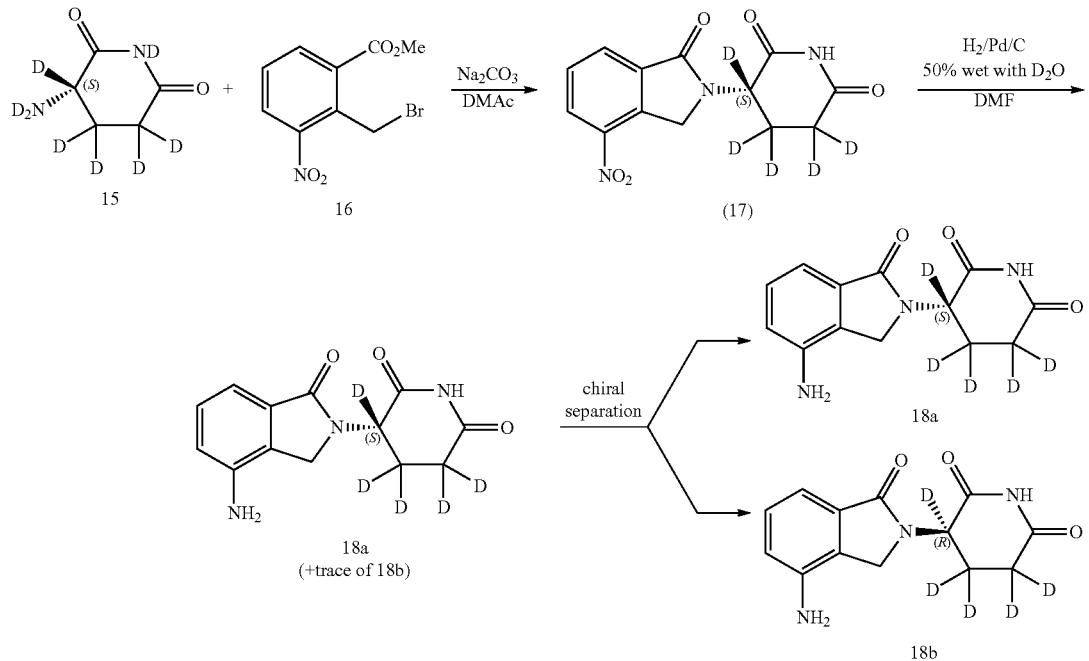

Step 1. Compound 17

Anhydrous N,N-dimethylacetamide (DMAc, 100 mL) was added to a mixture of 15 (5.1 g, 37.5 mmol, 1.01 equiv), 16 (10.1 g, 37.2 mmol, 1.0 equiv) and sodium carbonate (2.0 g, 18.8 mmol, 0.5 equiv) at room temperature. The reaction mixture was stirred for 18 hours, resulting in the formation of a grey solid in a purple solution. The reaction mixture was cooled to 0° C. and $D_2O$ (70 mL; Cambridge Isotopes, 99 atom % D) was added dropwise. The mixture was stirred at room temperature for 30 minutes and the solids were collected by filtration, washing with $D_2O$ (20 mL). The crude product was triturated with MTBE (100 mL), filtered, and dried, yielding 10.3 g (94%) of 17 as a white solid containing trace residual DMAc.

$^1$H NMR of the product indicated 8-9% proton incorporation at the chiral center of piperidine-2,6-dione ring.

Note: The % H incorporation did not appear to change in this step.

Note: The % ee was not checked at this step although a chiral LC method is available: Chiralpak AD 4.6×250 mm, 10 um, 50% hexane/50% isopropanol isocratic for 40 minutes at 0.6 mL/min

Step 2. Compound 18a

A suspension of 17 (7.4 g, 25.2 mmol) in anhydrous DMF (600 mL) was added to 10% Pd/C (740 mg, 50% wet with $D_2O$) and the mixture was hydrogenated at 50 psi of $H_2$ for 5 hours. The reaction mixture was then filtered through Celite, washing the Celite pad with DMF, and the filtrate was concentrated under reduced pressure (high vacuum pump) at 40° C., yielding a brown oil. The sides of the flask were rinsed with minimal THF. With stirring, a 1:1 mixture of heptanes:ethyl acetate (150 mL) was added dropwise, resulting in an off-white precipitate. The solids were collected by vacuum filtration, washing with heptanes. The solids were triturated with ethyl acetate (75 mL) at 50° C. for 4 hours to reduce the residual DMF, cooled to room temperature, filtered, and dried in a vacuum oven to yield 6.3 g (95%) of product 18a (containing a trace of its enantiomer 18b) as an off white solid.

$^1$H NMR indicated 5-6% H at the chiral center of the piperidinedione ring, and 4% residual DMF. Chiral LC showed this material to be 88% ee for the first eluting peak. (Chiralpak AD 4.6×250 mm, 10 um, 50% hexane/50% isopropanol isocratic for 40 minutes at 0.6 mL/min)

Note: The reaction was run in several batches ranging in scale from 4.0 g to 7.5 g with similar yields in each case.

Step 3. Separation of isomers 3-(4-amino-1-oxoisoindolin-2-yl)(piperidine-3,4,4,5,5-$d_5$)-2,6-dione (18a—first eluting peak) and (18b—second eluting peak)

A total of 20.0 g of 18 (88-90% ee) was subjected to chiral column chromatography—Column: CHIRALCEL® OZ-H 5 um, 30×250 mm. Eluent: 100% acetonitrile—yielding 17.5 g of 18a and 1.17 g of 18b:

18a (Form 1 D-(S)-lenalidomide):
>99% ee; contains 2.0% acetonitrile, 4.2% H at the chiral center; Retention Time: 9.95 min (Chiralpak AD 4.6×250 mm, 10 um, 50% hexane/50% isopropanol isocratic for 40 minutes at 0.6 mL/min).

18b:
23.3% ee; contains 2.8% acetonitrile, 32% H at the chiral center; Retention Time: 11.56 min (Chiralpak AD 4.6×250 mm, 10 um, 50% hexane/50% isopropanol isocratic for 40 minutes at 0.6 mL/min).

Example 2

Characterization of Form 1 D-(S)-lenalidomide

Figure 4:
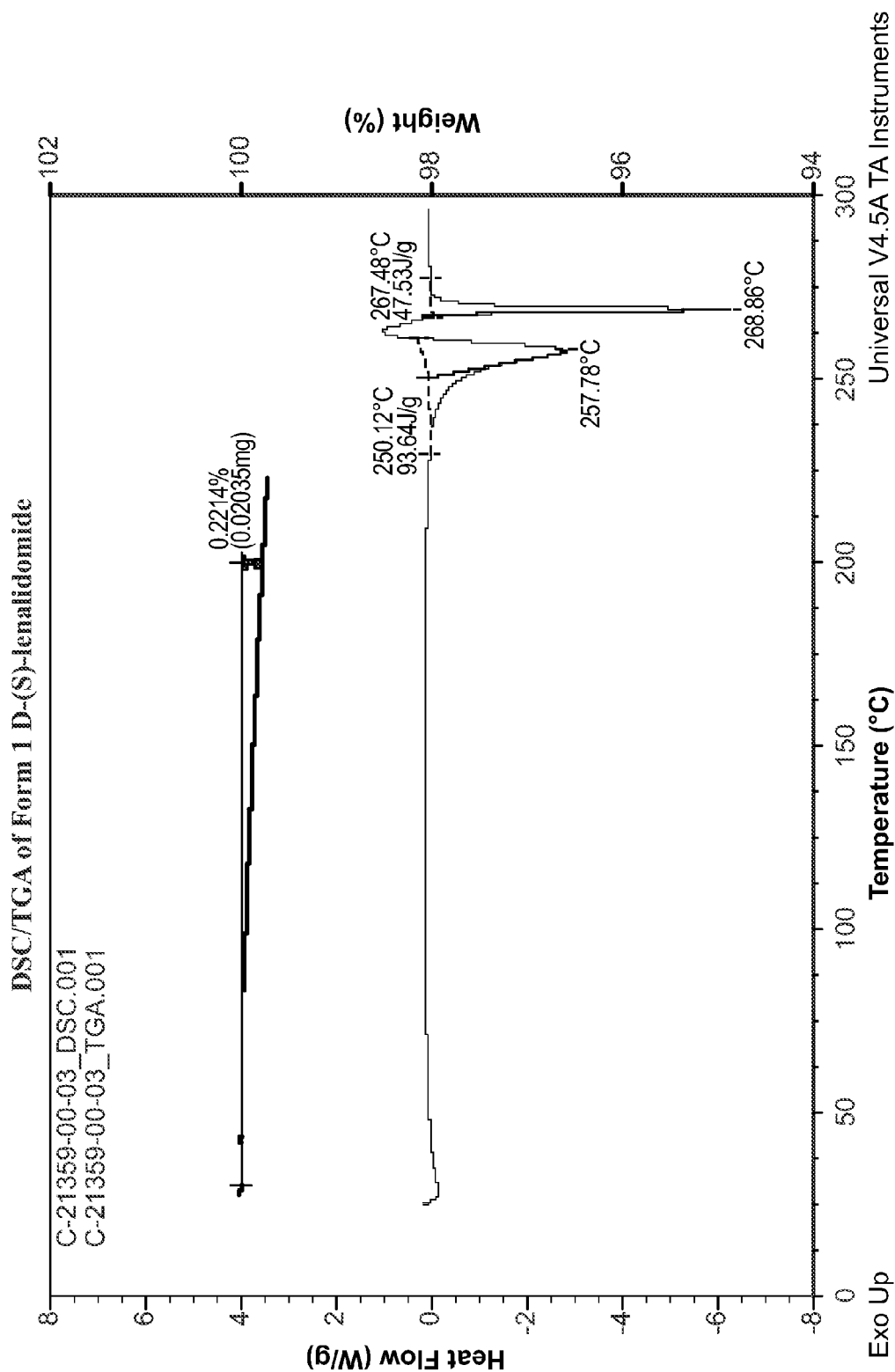
FIG. 4 is a plot showing DSC and TGA data for Form 1 of D-(S)-lenalidomide.
Figure 5:
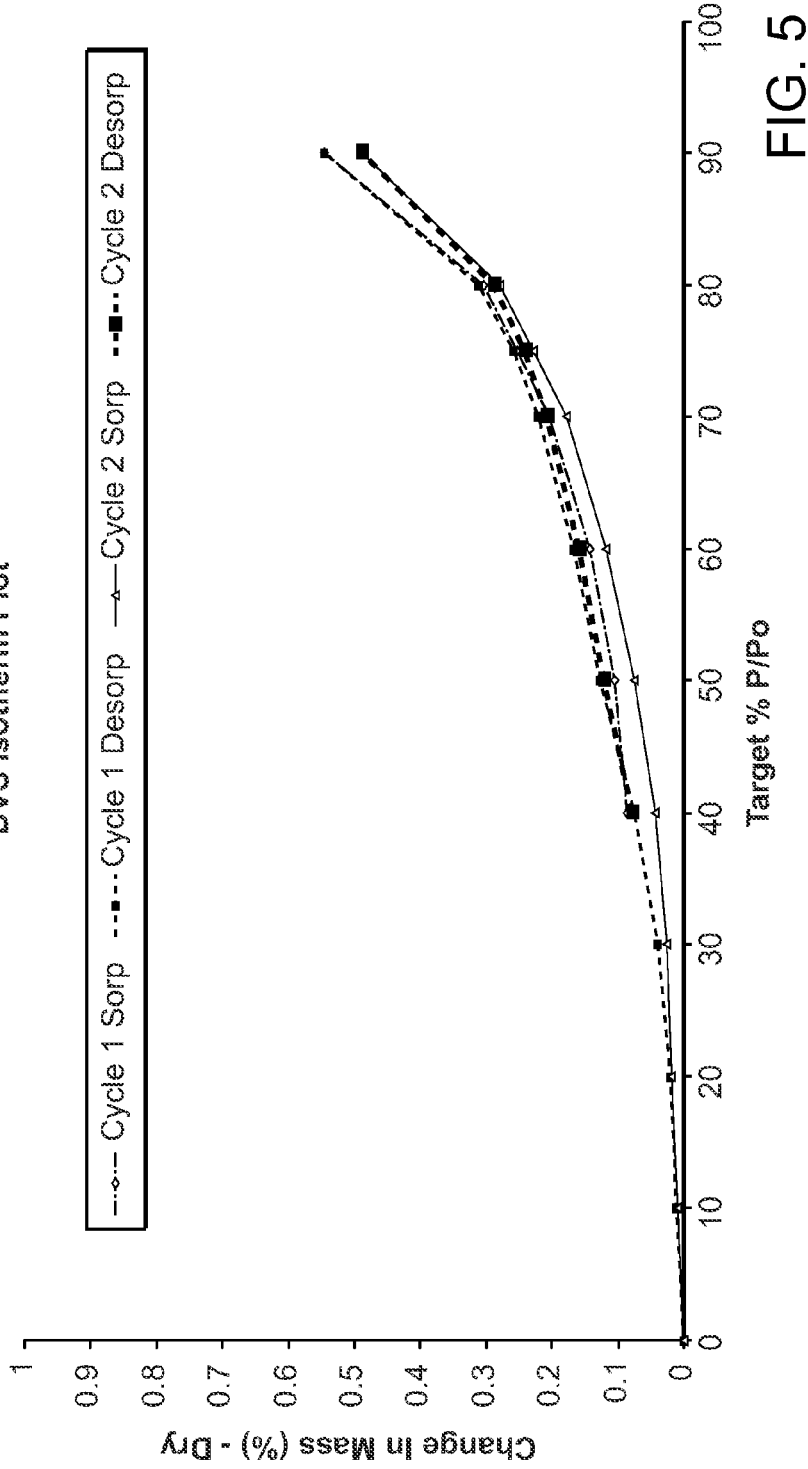
FIG. 5 is a DVS plot of Form 1 of D-(S)-lenalidomide.

Form 1 is a crystalline powder with a PXRD pattern indicated at FIG. 1. FT-Raman (FIG. 2) and FT-IR Spectra (FIG. 3) were also collected. As prepared, the particles exhibited plate-like habit, leading to a relatively high degree of preferred orientation. HPLC analysis indicated high purity of the material (>99.9% AUC). The TGA analysis showed ~0.2 wt. % loss upon heating the material up to 200° C. (FIG. 4), which indicates that Form 1 is a non-solvated form. The DSC trace of Form 1 shows an endothermic event at 250.1° C., immediately followed by an exotherm and an endotherm at ~267.5° C. (FIG. 4). The PXRD diffractogram of the material heated past the exothermic event (heating to 261° C. followed by isothermal hold for 7 min) indicates a racemization of D-(S)-lenalidomide, as confirmed by chiral HPLC analyses of a reference material. DVS analysis revealed that Form 1 is non-hygroscopic (<0.65 wt. % gain between 0-90% RH) (FIG. 5) and PXRD showed it to be physically stable at 40° C./75% RH for 6 days. This conclusion is based on two simultaneously run experiments. In one experiment, Form 3 was exposed to 40° C./75% RH. Within 6 days about half of the solid converted to Form 1. In the second experiment Form 1 was exposed to the same conditions and the PXRD pattern of the product after 6 days indicated Form 1 as the major component, with only a trace of Form 3 being formed, as indicated by the appearance of a small peak at 9.8 2 theta in the PXRD spectrum after 6 days. Moreover, even this formation of Form 3 may have been at least in part the result of condensation inside of the RH chamber towards the end of the experiment, as a result of which Form 1 became slightly wet.

Example 3

Solubility of Form 1 D-(S)-lenalidomide

Solubility of Form 1 was visually estimated in an array of different solvents. The solubility was measured at 20° C. by dosing small aliquots of the solvent into a fixed amount of the Form 1 (10.0 mg) until the dissolution point or a maximum volume (10.0 mL) was reached. Where applicable, the undissolved solids were analyzed by PXRD to verify crystal form. The data are shown in and indicate that the solubility of Form 1 to be relatively low in water and common organic solvents, (<6 mg/mL), very high in dimethylsulfoxide (DMSO; >400 mg/mL), and moderate in water- or DMSO-containing binary solvent systems.

Example 4

Preparation of Form 2 D-(S)-lenalidomide 100 mg of Form 1 was weighed into a 20-mL vial. Acetonitrile:water (50:50% vol.; 5.0 mL) was added and the suspension was stirred at room temperature until solids dissolved (~15 min). The obtained solution was filtered into a clean 20-mL vial using a syringe equipped with a 0.45 μm filter. The filtrate was frozen in a liquid nitrogen bath and subjected to lyophilization for 24 hours resulting in the production of the hydrate referred to herein as Form 2.

Example 5

Characterization of Form 2 D-(S)-lenalidomide

PXRD (FIG. 6) and PLM microscopy analyses indicate Form 2 to be partially crystalline and phase-impure with amorphous content. Thermal analyses confirmed that the material loses 4.3% wt. upon heating up to 160° C. (FIG. 8). IR analysis of the volatile component released upon heating confirmed water. The loss of water corresponds to broad endothermic (50-100° C.) and exothermic (120-160° C.) events on the DSC trace (FIG. 8), indicating potential dehydration and crystallization, respectively. An FT-Raman spectrum is provided at FIG. 7. Form 2 is physically stable for at least 24 hrs. Form 2 converts to a mixture of Forms 1 and 3 within 3 weeks of storage in an closed vial at room temperature and Form 3 upon stirring it in water for 12 hr at 5° C.

Example 6

Preparation of Form 3 D-(S)-lenalidomide from Form 1

Form 1 of D-(S)-lenalidomide (20 mg) was weighed into a 2-mL vial containing a stir bar. Water (1.0 mL) was added, and the sample was stirred at 20° C. for 20 hr. The solid was isolated on a Büchner funnel and air-dried for 4 hours Example 7

Preparation of Form 3 D-(S)-lenalidomide from Form 2

Form 2 (50 mg) was combined with water (1.0 mL) and the suspension was stirred at 5° C. for 20 hours. The solid was isolated on a Büchner funnel and air-dried for 4 hours.

Example 8

Characterization of Form 3 D-(S)-lenalidomide

PXRD (FIG. 9) and PLM analyses of Form 3 indicate it is a crystalline material. Thermal analyses confirmed that the material loses 12% wt. upon heating up to 160° C. (FIG. 11). Infrared spectral analysis of the volatile component released upon heating confirmed water. The weight loss closely corresponds to a dihydrate composition (theoretical % wt. of 2 equivalents of water=12.7% wt.). The weight loss corresponds to a sharp dehydration endotherm (98.6° C.) followed by a melting endotherm (259.5° C.) on the DSC trace (FIG. 11). An FT-Raman spectrum is provided at FIG. 10 and DVS data at FIG. 12.

Example 9

Preparation of Amorphous D-(S)-Lenalidomide

Form 1 (10 mg) was weighed into a 2-mL vial. 0.5 ml of a 45:45:10% by volume mixture of 1,4-dioxane:acetonitrile:

water (45:45:10 vol. %; 0.5 mL) was added and the suspension was stirred at room temperature until solids dissolved (~15 min). The obtained solution was filtered into a clean 2-mL vial using a syringe equipped with a 0.45 μm filter. The solution was frozen in a liquid nitrogen bath and lyophilized for 24 hours.

Example 10

Preparation of Amorphous D-(S)-Lenalidomide

Form 1 (10.0 mg) was weighed into a 20-mL vial and dissolved in methanol (10.0 mL). The solution was filtered into a clean 2-mL vial using a syringe equipped with a 0.45 μm filter. The filtrate was rotovapped for 20-30 min at 65° C.

Example 11

Characterization of Amorphous D-(S)-lenalidomide Obtained by Lyophilization

PXRD (FIG. 13A) and PLM analyses of the material confirmed its amorphous nature. Thermal analyses showed a 15.1% weight loss upon heating up to 180° C. (FIG. 14). Infrared spectral analysis of the volatile component released upon heating confirmed 1,4-dioxane. The DSC trace shows broad and poorly pronounced endotherms between ~45-100° C., followed by an exotherm at ~135.3° C., and a melting endotherm at 244.1° C. on the DSC trace. The PXRD analysis of the amorphous material heated past the exothermic event indicated Form 1. HPLC analysis of the lyophilized amorphous material indicated high chemical purity (>99.9% AUC). The lyophilized amorphous material exhibited very low bulk density, leading to difficulties at physical handling such as transfer and weighing.

Example 12

Characterization of Amorphous D-(S)-lenalidomide Obtained by Rapid Evaporation

Rapid evaporation of methanol from the solution of Form 1 in Example 10 produced a glassy, tacky material, which was found to be amorphous, by PXRD (FIG. 13B) and PLM. The HPLC analysis of this material indicated a slight degradation measuring 2.5% AUC.

Example 13

Solubility of Form 1 D-(S)-lenalidomide

Solubility of Form 1 was visually estimated in an array of diverse solvents. The solubility was measured at 20° C. by dosing small aliquots of the solvent into a fixed amount of Form 1 (10.0 mg) until the dissolution point or a maximum volume (10.0 mL) was reached. Where applicable, the undissolved solids were analyzed by PXRD to verify crystal form. The data are shown in Table 2 and indicate that the solubility of Form 1 is relatively low in water and common organic solvents, (<6 mg/mL), very high in dimethylsulfoxide (DMSO; >400 mg/mL), and moderate in water- or DMSO-containing binary solvent systems.

TABLE 2

| # | Solvent | Solubility at RT | Solubility at 40° C. | Residual Solid |
|---|---|---|---|---|
| 1 | DMSO | >400 | * | * |
| 2 | Acetonitrile: 10% vol. Water | 14-17 | * | * |
| 3 | Acetonitrile: 10% vol. DMSO | 10-30 | * | * |
| 4 | 2-Propanol: 10% vol. DMSO | 1-10 | * | * |
| 5 | Methanol: 5% vol. Water | 1-10 | * | * |
| *6 | Methanol: 10% vol. Water | 1-10 | * | * |
| 7 | Water | 1-6 | * | * |
| 8 | Methanol | 1-6 | * | * |
| 9 | Acetonitrile | 1-6 | * | * |
| 10 | Acetone | 1-6 | * | * |
| 11 | Tetrahydrofuran | 1-6 | * | * |
| 12 | 1,4-Dioxane | <1 | >6 | Form 1 |
| 13 | 2-Propanol | <1 | <1 | Form 1 |
| 14 | Dichloromethane | <1 | <1 | Form 1 |
| 15 | Ethyl Acetate | <1 | <1 | Form 1 |
| 16 | Toluene | <1 | <1 | Form 1 |
| 17 | Heptane | <1 | <1 | Form 1 |

Example 14

Relative Stability of Forms 1 and 3 in Water

A series of experiments were conducted to assess the relative stability of Forms 1 and 3. The studies involved suspending Form 1 in aqueous/organic mixtures with water activities ($\alpha_w$) between 0.2-1.0 and stirring the suspensions at ambient temperature for 4 hours. The suspensions were each seeded with a small amount of Form 3 (~1 mg) and stirred until a complete form conversion occurred. The results from the study are summarized in Table 3 and show that at 20° C. Form 1 is more stable at $\alpha_w$<0.7, above which Form 3 is more stable. At lower temperatures (5, and 7° C.) Form 1 is more stable at $\alpha_w$<0.5.

TABLE 3

| Solvent | Approximate Water Activity | Temperature [° C.] | Produced Crystal Form |
|---|---|---|---|
| Water | 1.0 | 20 | Form 3 |
| | | 5 | Form 3 |
| 1,4-Dioxane:Water 90:10% vol. | 0.7 | 20 | Form 1 |
| | | 5 | Form 3 |
| 1,4-Dioxane:Water 96.5:3.5% vol. | 0.5 | 20 | Form 1 |
| | | 7 | Form 1 |
| 1,4-Dioxane:Water 99:1% vol. | 0.2 | 20 | Form 1 |

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. Form 1 of D-(S)-lenalidomide whose x-ray powder diffraction patterns is substantially the same as that found in FIG. 1.

2. The form of claim 1 whose Raman spectrum is substantially the same as that found in FIG. 2.

3. The form of claim 1 having a melting temperature at about 250° C.

* * * * *